United States Patent [19]
Abele et al.

[11] Patent Number: 5,496,311
[45] Date of Patent: Mar. 5, 1996

[54] PHYSIOLOGIC LOW STRESS ANGIOPLASTY

[75] Inventors: John E. Abele, Concord, Mass.; Charles D. Lennox, Hudson, N.H.

[73] Assignee: Boston Scientific Corporation, Watertown, Mass.

[21] Appl. No.: 236,393

[22] Filed: May 2, 1994

Related U.S. Application Data

[63] Continuation of Ser. No. 146,452, Nov. 1, 1993, abandoned, which is a continuation of Ser. No. 965,518, Oct. 23, 1992, abandoned, which is a continuation of Ser. No. 809,237, Dec. 17, 1991, abandoned, which is a continuation of Ser. No. 589,346, Sep. 27, 1990, abandoned, which is a continuation-in-part of Ser. No. 404,483, Sep. 8, 1989, abandoned, which is a continuation-in-part of Ser. No. 263,815, Oct. 28, 1988, Pat. No. 4,955,377.

[51] Int. Cl.$^6$ .................................................. A61M 29/02
[52] U.S. Cl. .................................................. 606/28
[58] Field of Search .................................. 606/27–31, 41, 606/42, 192, 194

[56] References Cited

U.S. PATENT DOCUMENTS

| 612,724 | 10/1898 | Hamilton . |
|---|---|---|
| 2,032,859 | 3/1936 | Wappler . |
| 2,043,083 | 6/1936 | Wappler . |
| 2,078,686 | 4/1937 | Rowe . |
| 2,126,070 | 8/1938 | Wappler . |
| 3,661,148 | 5/1972 | Kolin . |
| 3,866,699 | 2/1975 | Johnson . |
| 4,190,053 | 2/1980 | Sterzer . |
| 4,195,637 | 4/1980 | Gruntzig et al. . |

(List continued on next page.)

FOREIGN PATENT DOCUMENTS

| 0182689 | 5/1986 | European Pat. Off. . |
|---|---|---|
| 0205851 | 12/1986 | European Pat. Off. . |
| EP-A-0205851 | 12/1986 | European Pat. Off. . |
| 251745 | 6/1987 | European Pat. Off. . |
| 0315982 | 5/1989 | European Pat. Off. . |
| EP-A-0315982 | 5/1989 | European Pat. Off. . |
| 0311458 | 12/1989 | European Pat. Off. . |
| 718993 | 1/1932 | France . |
| 342419 | 2/1931 | United Kingdom . |
| 2154761 | 9/1985 | United Kingdom . |
| WO82/00768 | 3/1982 | WIPO . |
| WO-A-8905609 | 6/1989 | WIPO . |
| WO-A-8905165 | 6/1989 | WIPO . |
| WO8905165 | 6/1989 | WIPO . |
| WO8905609 | 6/1989 | WIPO . |
| WO-A-9004365 | 5/1990 | WIPO . |
| WO9004365 | 5/1990 | WIPO . |
| WO91/03996 | 9/1990 | WIPO . |
| WO90/14046 | 11/1990 | WIPO . |

OTHER PUBLICATIONS

Abele, "Balloon Catheters and Transluminal Dilitation: Technical Considerations", *AJR* 135:901–906 (Nov. 1980).

Astrahan et al., "Temp Meas. from MW Antenna" (Excerpt) (Mar. 3, 1988).

Becker et al., "Radiofrequency Balloon Angioplasty Rationale and Proof of Principle", *Investigative Radiology* 23:810–817 (Nov. 1988).

Bresovich et al., "A Practical System for Clinical Radiofrequency Hyperthermia", *J. Radiation Oncology Bio. Phys.* 7:423–430 (1981).

(List continued on next page.)

*Primary Examiner*—Max Hindenburg
*Attorney, Agent, or Firm*—Fish & Richardson

[57] ABSTRACT

Systems and methods for dilation of a body lumen, using an expandable dilatation catheter to simultaneously heat and apply pressure to tissue of the lumen and to expand and dilate the lumen including means constructed to produce and/or detect physiological response of the heated tissue to applied pressure.

52 Claims, 12 Drawing Sheets

U.S. PATENT DOCUMENTS

| | | |
|---|---|---|
| 4,197,860 | 4/1980 | Sterzer. |
| 4,204,549 | 5/1980 | Paglione. |
| 4,207,874 | 6/1980 | Choy. |
| 4,240,445 | 12/1980 | Iskander et al.. |
| 4,311,154 | 1/1982 | Sterzer et al.. |
| 4,323,071 | 4/1982 | Simpson et al.. |
| 4,346,716 | 8/1982 | Carr. |
| 4,370,982 | 2/1983 | Reilly. |
| 4,411,648 | 10/1983 | Davis et al.. |
| 4,446,867 | 5/1984 | Leveen et al.. |
| 4,446,874 | 5/1984 | Vaguine. |
| 4,470,407 | 9/1984 | Hussein. |
| 4,512,762 | 4/1985 | Spears. |
| 4,528,991 | 7/1985 | Dittmar et al.. |
| 4,552,194 | 11/1985 | Norman. |
| 4,612,940 | 9/1986 | Kasevich et al.. |
| 4,641,649 | 2/1987 | Walinsky et al.. |
| 4,643,186 | 2/1987 | Rosen et al.. |
| 4,646,737 | 3/1987 | Hussein et al.. |
| 4,651,738 | 3/1987 | Demer et al.. |
| 4,662,368 | 5/1987 | Hussein et al.. |
| 4,662,383 | 5/1987 | Sogawa et al.. |
| 4,700,716 | 10/1987 | Kasevich et al.. |
| 4,709,698 | 12/1987 | Johnston et al. ........................ 604/114 |
| 4,747,405 | 5/1988 | Leckrone. |
| 4,754,752 | 5/1988 | Ginsberg et al.. |
| 4,773,899 | 9/1988 | Spears. |
| 4,781,192 | 11/1988 | Demer. |
| 4,799,479 | 1/1989 | Spears ........................................ 606/28 |
| 4,955,377 | 9/1990 | Lennox et al.. |
| 4,998,933 | 3/1991 | Eggers et al.. |
| 5,009,662 | 4/1991 | Wallace et al.. |
| 5,019,075 | 5/1991 | Spears. |
| 5,032,113 | 7/1991 | Burns. |
| 5,035,694 | 7/1991 | Kasprzyk et al. ........................ 606/28 |
| 5,041,089 | 8/1991 | Mueller et al.. |
| 5,057,106 | 10/1991 | Kasevich et al. ........................ 606/33 |
| 5,061,267 | 10/1991 | Zeiher. |
| 5,092,841 | 3/1992 | Spears. |
| 5,114,423 | 5/1992 | Kaspryzk et al.. |
| 5,151,100 | 9/1992 | Abele et al. ............................. 606/28 |
| 5,190,540 | 3/1993 | Lee ........................................... 606/28 |

OTHER PUBLICATIONS

John A. Abele, "Basic Technology of Balloon Catheters", *Percutaneous Transluminal Angioplasty,* 1983 pp. 32–36.

Kaltenbach et al., "Prolonged Application of Pressure in Transluminal Coronary Angioplasty", *Catherization and Cardiovascular Diagnosis,* pp. 213–219, 1984, vol. 10.

H. Ward, "Laser Recannalization of Atheromatous Vessels Using Fiber Optics", *Lasers in Surgery and Medicine,* vol. 4, pp. 353–363, 1984.

Jenkins et al., "Laser Balloon Angioplasty: Effect of Exposure Duration on Shear Strength of Welded Layers of Postmortem Human Aorta", *Lasers in Surgery and Med.,* vol. 8, pp. 392–396, 1988.

Anand et al., "Laser Balloon Angioplasty: Effect of Constant Temperatur Versus Constant Power on Tissue Weld Strength", *Lasers in Surgery and Medicine,* vol. 8, pp. 40–44, 1988.

J. Richard Spears, "Sealing", *Cardiovascular Laser Therapy,* pp. 178–199, 1989.

Crea et al., "Percutaneous Laser–Assisted Coronary Angioplasty, " *Lancet* 2:214–15 (Jul. 5, 1986).

Cumberland et al., "Percutaneous Laser–Assisted Coronary Angioplasty," *Lancet 2:215 (Jul. 5, 1986).*

Fanelli et al., "Restenosis Following Coronary Angioplasty," *Amer. Heart J.* 119:357–368 (Feb. 1990.

Gruntzig et al., "Technique of Percutaneous Transluminal Angioplasty with the Grunzig Balloon Catheter," *AJR* 132:547–552 (Apr. 1979).

Haines et al., "The Impedance Rise During Radiofrequency Ablation in Vivo is Prevented by Maintaining an Electrode Tip Temperature Below the Boiling Point," *Circulation* 80:0161 (Oct. 1989).

Hiehle et al., "Nd–YAG Laser Infusion of Human Atheromatous Plaque–Arterial Wall Separations In Vitro," *Am. J. Cardiol.* 56:953–57 (1985).

Hoher et al., "Percutaneous Coronary 'Hot–Tip' Angioplasty in Man Using a Radiofrequncy Catheters," *Circulation* (Supp. II) 78:11–296, 1179 (Oct. 1988) (abstract).

Hoffman et al., "Temperature–Controlled Impedance–Guided Radiofrequency Catheter Ablation in Swine", *Circulation* 80:0170 (Oct. 1989) (Supp. II) (abstract).

Jain et al., "In Vivo Assessment of Vascular Digitation During Percutaneous Transluminal Coronary Angioplasty", *Am. J. Cardiol.* 60:988–992 (Nov. 1, 1987).

Jenkins et al., "Laser Balloon Angioplasty vs. Balloon Angioplasty in Normal Rabbit Italic Arteries," *Circulation IV–47, 0188 (1987) (abstract).*

Kaplan et al., "Thermal Angioplasty with a Biopolar Radiofrequency Balloon System," *Circulation* 78:II–503 2009 (Supp II) (1988) (abstract).

Kumpe, "Percutaneous Dilitation of an Abdominal Aortic Stenosis", *Radiology,* 141:536–538 (Nov. 1981).

Lee et al., "Thermal Compression and Molding of Atherosclerotic Vascular Tissue With Use of Radiofrequency Energy: Implications for Radiofrequency Balloon Angioplasty," *JACC* 13:1167–75 (Apr. 1989).

Lee et al., "Blood Enhancement of thermal injury to Carciovascular Tissues is Not Specific to Laser Energy," *Clin. Res.* 36:293A (Apr. 1988) (abstract).

Lee et al., "Thermal Remodeling of Human Atherosclerotic Plaque Using Radiofrequency Energy," *Clin. Res.* 36:2693A (Apr. 1988) (abstract).

Lee et al., "Thermal Effects of Laser and Electrical Discharge on Cardiovascular Tissue: Implications for Coronary Artery Recanalization and Endocardial Ablation," *JACC* 8:193–200 (Jul. 1986).

Litvack et al., "Percutaneous 'Hot–Tip' Angioplasty in Man By a Radio Frequency Catheter System," *JACC* 11:108A (Feb. 1988) (abstract).

Litvack et al., "'Hot–Tip' Angioplasty by a Novel Radiofrequency Catheter," *Circulation* IV–47, 0185 (1987) (abstract).

Myler et al., "High and Low Poer Thermal Laser Angioplasty For Total Occlusions and Restenosis in Man," *Circulation* 76:IV–230, 0196 (Supp. IV) (Oct. 1987) (abstract).

Protell et al, "Computer Assisted electrocoagulation Bipolar v. Monopolar in the Treatment of Experimental Gastric Ulcer Bleeding", Abstract at the Meeting of the American Gastroenterological Association (May 21–23, 1979).

Samaras et al., "Correction of Microwave–Induced Thermister Sensor Errors", *Med. Phys.* 10:326–33s (May/Jun. 1983).

Sanborn et al., "Percutaneous Laster Thermal Angioplasty: Initial Results and 1–Year Follow–Up in 129 Femoropopliteal Lesions," *Circulation* 168:121–25 (Jul. 1988).

Sanborn et al., "Laser Thermal Angioplasty As An Adjunct To Peripheral Balloon Angioplasty: One Year Follow–Up Results," *Circulation* 76:IV–230, 0917 (Supp.IV) (Oct.

1987) (abstract).

Sanborn et al., "Angiographic ad Histologic Consequences of Laser Thermal Angioplasty: Comparison With Balloon Angioplasty," *Circulation* 75:1281–86 (Jun. 1987).

Sanborn et al., "Percutaneous Coronary Laser Thermal Angioplasty," *JACC* 8:1437–40 (Dec. 1986).

Schwartz et al., "Microwave Balloon Angioplasty: Histolic Effects of 10 GHZ Midrowave Energy on Human Aorta and Myocardium," *Circulation* 80:1013 (Oct. 1989) (Supp. II) (abstract).

Sigel et al., "The Mechanism of Blood Vessel Closure by High Frequency Coagulation", *Surgery, Gynecology and Obstertrics* 823–831 (Oct. 1985).

Sinclair et al., "Thrombogenic Potential of Dog Coronary Artery After Laser Balloon Angioplasty," Circulation 80:104 (Oct. 1989) (Supp. II) (abstract).

Sinclair et al., "Effect of Laser Balloon Angioplasty on Normal Dog Coronary Arteries in Vivo," *JACC* 11:108A (Feb. 1988) (abstract).

Waller et al., "Coronary Balloon Angioplasty Restenosis: Pathogenesis and Treatment Strategies from a Morphological Perspective," *J. Intervent. Cardiol.* 2:167–178 (1989).

Zeiher et al., "'Hot Balloon' Angioplasty Reduces Platelet Deposition at the Site of Injury," *Circulation* 78:1182 (Supp. II) (Oct. 1988).

Zeiher et al., "A Prototype RF Heated Hot Balloon PTCS Catheter: Design Parameters and In Vitro Tissue Studies", *Circulation* 78:1181 (Supp. II) (Oct. 1988).

Zeiher et al., "Radiofrequency 'Hot Balloon' Angioplasty: Immediate Arterial Remodeling and Effects on Restenosis in the Arteriosclerotic Rabbit," *Circulation* 80:1018 (Supp. II) (Oct. 1989) (abstract).

Zollikofer et al., "Results of Animal Experiments With Balloon Dilatation", Percutaneous Transluminal *Angioplasty,* copyright, Springer Verlag, Berlin, 1983, Chapter 12 pp. 60–72.

John E. Abele, "Balloon Catheters and Transluminal Dilatation: Technical Considerations", AJR 135 Nov., 1980, pp. 901–906.

Small, "Propression and Regression of Atherosclerotic Lesions: Insights from Lipid Physical Biochemistry," Arteriosclerosis 8:103–129 (Mar./Apr. 1988).

Smith, "Progression and Regression of Atherosclerotic Lesions: Insights from Lipid Physical Biochemistry," Arteriosclerosis 8:103–129 (Mar./Apr. 1988).

Spears et al., "Coronary *Laser* Balloon Angioplasty," *Cardiac Chronicle* 4:1–5 (Jan. 1990).

Spears et al., "Percutaneous Coronary Laser Balloon Angioplasty: Preliminary Results of a Multicenter Trial," *JACC* 13:61a (Feb. 1989) (abstract).

Spears et al., "Laser Balloon Angioplasty: Initial Clinical Percutaneous Coronary Results," *Circulation* 78:II–296, 1180 (Supp. II) (Oct. 1988) (abstract).

Spears, "Percutaneous Transluminal Coronary Angioplasty Restenosis: Potential Prevention With Laser Balloon Angioplasty", *Am. J. Cardio.* 60:61B–64B (Jul. 31, 1987).

Spears et al., "Reversible Plaque Optical Property Changes During Repetitive CW ND:YAG Laser Exposure." *Circulation* IV–47, 0187 (1987) (abstract).

Stroh et al., "Experimental Argon Laser Thermal Angioplasty as an Adjunct to Balloon Angioplasty," *JACC* 11:108a (Supp.A) (Feb. 1988) (abstract).

Szwarnowski, "A Thermometer for Measuring Temperatures in the Presence of Electromagnetic Fields", *Clin. Phys. Physiol. Meas.* 4:79–84 (1983).

Trembly, "Practical Embedded Insulated Antenna for Hyperthermia", *Proceedings of the Tenth Annual Northeast Bioengineering Conferences* 105:1–8 (Mar. 15–16, 1982).

Waller, "Crackers, Breakers, Stretchers, Drillers, Scrapers, Showers, Burners, Welders, and Melters'—The Future Treatment of Atherosclerotic Coronary Artery Disease A clinical–Morphologic Assessment," *JACC* 13:969–87 (Apr. 1987).

PHYSIOLOGIC LOW STRESS ANGIOPLASTY

This is a continuation of application Ser. No. 08/146,452, filed Nov. 1, 1993, now abandoned which is a continuation of application Ser. No. 07/965,518, filed Oct. 23, 1992, now abandoned, which is a continuation of application Ser. No. 07/809,237, filed Dec. 17, 1991, now abandoned, which is continuation of application Ser. No. 07/589,346, filed Sep. 27, 1990, now abandoned, which is a continuation-in-part of application Ser. No. 07/404,483, filed Sep. 8, 1989, now abandoned, which is a continuation-in-part of application Ser. No. 07/263,815, filed Oct. 28, 1988, now U.S. Pat. No. 4,955,377.

FIELD OF THE INVENTION

This invention relates to balloon catheters and similar devices useful to apply heat within a patient's body, e.g. for angioplasty, hyperthermal treatment of tumors, and other medical procedures.

BACKGROUND OF THE INVENTION

Stenoses in body lumens are often treated by balloon catheter dilatation, sometimes followed or accompanied by the application of heat. A balloon at the end of a catheter is positioned at the obstruction (in a blood vessel, typically plaque) and inflated. The pressure of the balloon against the wall of the lumen or obstructing material supplies a force to widen the lumen. A problem that sometimes occurs with dilatation is damage to the lumen tissue or reocclusion because of reaction of the lumen tissue to the dilatation. An example is intimal hyperplasia. Also, plaque material in arteries sometimes fractures or cracks under pressure of the angioplasty balloon, leaving rough surfaces that encourage further deposits, thrombosis and reocclusion.

SUMMARY OF THE INVENTION

It is an object of the present invention to provide an improved apparatus and method for the treatment of stenoses in internal body lumens by use of pressure and heat in a novel way that can help to overcome these and other problems.

The invention features a system for dilation of a body lumen and a method of using the system, employing an expandable dilatation catheter constructed to simultaneously heat and apply pressure to the tissue of the lumen and to expand and dilate the lumen, and means constructed to detect physiological response of the heated tissue to applied pressure. The means includes catheter control means responsive to the detected behavior of the tissue to control the catheter. Preferred embodiments have the following features. The means to detect physiological response is constructed to detect yielding behavior of the heated lumen tissue contacted by the catheter, and the catheter control means is responsive thereto. The means to detect physiological response is constructed to detect change in the heat transfer characteristic of the tissue contacted by the catheter and the catheter control means is responsive thereto. Means are provided to prevent contraction of the catheter during cooling of the lumen tissue following heating.

The catheter control means includes a microprocessor and is arranged to receive feedbacks indicative of temperature and pressure applied by the catheter, the control means adapted to regulate heating and pressure applied by the catheter on the basis of the feedbacks and an algorithm implemented by the microprocessor.

A timing means is provided, constructed and arranged to provide timing of the duration of the dilatation based upon the physiological response to the heat and applied pressure.

Preferred embodiments also have the following features. A catheter is employed that is constructed to heat the lumen tissue by conductive heat transfer through a wall of the catheter exposed to the lumen tissue. The catheter is a balloon catheter fillable with an electrically conductive liquid and the associated heating means for producing the heat comprises rf electrodes within the balloon and means to apply rf energy thereto in a manner to heat the liquid by $I^2R$ losses. The catheter is a fluid inflatable catheter, and the catheter control means is an inflation control means. A means to detect physiological response comprises a pressure sensor constructed and arranged to sense the fluid pressure in the catheter and detect reduction in the pressure that results due to pressure-responsive yielding behavior of the heated lumen tissue, the catheter control means being responsive to the detected change in pressure, to increase the volume of inflation of the catheter. Alternatively, a means to detect physiological response includes a volume sensor indicating change in the inflated volume of the inflatable catheter.

The inflation control means includes a servo motor-driven syringe pump, preferably including a position transducer for measuring the displacement of the syringe pump, thereby to indicate the volume of the inflatable catheter. Means are associated with the inflatable catheter to prevent deflation of the catheter during cooling of the lumen tissue following heating, preferably the means to prevent deflation being a fluid check valve. The inflatable catheter includes means for measuring the temperature of fluid within the inflatable catheter.

Also, preferred embodiments have the following features. The catheter control means comprises a controller constructed to receive signals indicative of the pressure or volume and the temperature of the inflatable catheter, the controller constructed to control the inflation and temperature in response to the signals, for further treatment.

The system includes display means to provide a read-out indicative of the physiological response of the tissue under treatment. The read-out indicates pressure applied by the catheter, heating by the catheter and volume of the catheter.

In another aspect of the invention, a system for dilation of a body lumen is provided comprising an inflatable dilatation ballon catheter and associated heating means arranged to simultaneously apply pressure to the tissue and heat via conductive heat transfer from the balloon to lumen tissue, and means constructed to detect physiological response of the heated tissue to applied pressure. The means including catheter control means responsive to the detected behavior of the tissue to control the catheter.

Preferred embodiments of this aspect of the invention have the following features. The catheter control means is adapted to increase the inflation of the balloon in reaction to detected yielding behavior of the lumen tissue contacted by the catheter. The means to detect physiological response is constructed to detect change in the heat transfer characteristic of the lumen tissue and to reduce the heating on the basis of such detected change. The catheter control means comprises a under control of a programmed microprocessor. The program of the microprocessor is adapted to increase an inflation set point of an inflation pressure controller in reaction to feedback from the catheter indicating yielding behavior of the heated lumen tissue. The microprocessor is programmed to produce heating of lumen tissue at a pressure below normal dilatation pressure.

In the method for dilation of a body lumen employing the system just described a number of features are preferred. The method is used to remodel a lumen. The method is used for angioplasty. A step of the procedure is terminated after a measured period from the time of detection of a physiological response. Timing means are employed, constructed and arranged to provide timing of the duration of the dilatation based upon the physiological response to the heat and applied pressure. The initial temperature of heating is between about 50° C. and 70° C. The catheter is a balloon catheter filled with liquid and the wall of said lumen is heated by heating the liquid, with heat transfer by conduction from the liquid across the wall thickness of the balloon to the tissue of the wall with which the balloon is engaged.

The liquid within the balloon is electrically conductive and the liquid is heated by $I^2R$ losses as a result of radio frequency electric currents applied to the liquid.

In another aspect, the invention features a method of angioplasty, in which a catheter is provided having a liquid-expansible dilatation balloon and means for controllably providing heated liquid within the balloon to enable conductive heat transfer from the liquid, through the wall of the balloon. The catheter is inserted into a region of a blood vessel narrowed by plaque or stenotic tissue, and the balloon is inflated to an initial subdilatation pressure sufficient to cause the balloon to engage the wall surface of the narrowed vessel in a conductive heat transfer relationship without substantially displacing the wall of the vessel. The temperature of the engaged vessel wall is increased by conductive heat transfer from heated liquid within the balloon while controlling the inflating pressure, the temperature of the liquid within the balloon and the duration of treatment to cause a physiological response in which the heated wall of the vessel yields to said pressure of said dilitation balloon as a result of softening of the wall produced by conductive heat transfer. Dilatation of the vessel can thus occur under relatively low stress conditions.

In preferred embodiments, the pressure in the balloon is about 2 atmospheres or less. Controlling comprises maintaining the temperature in the range of about 60° to 65° C. The subdilatation pressure is initially maintained such that the flow of blood is substantially blocked but without widening the vessel visibly to the naked eye when observing the vessel by fluoroscopy. The initially maintained subdilatation pressure is such that the vessel does not widen by more than about 10%.

In preferred embodiments, the method includes maintaining inflation of the balloon while reducing the temperature of the balloon after dilatation of the vessel. Increasing the balloon temperature to a final temperature between 50° C. and 70° C. within about 10 to 15 seconds of the inflation to the subdilatation pressure, and holding the final temperature for about up to about 60 seconds. Thereafter, the balloon temperature is reduced while maintaining the inflation by terminating the heating of the fluid and allowing the balloon to cool for about 15 to 30 seconds. The inflation pressure is controlled to prevent exceeding the subdilatation pressure.

In preferred embodiments the progress of the angioplasty is monitored, and the temperature, pressure or duration of treatment is controlled in response to the rate of change in the diameter of the vessel. The pressure, temperature of the balloon or duration of treatment is reduced if a rapid change in the diameter of the vessel indicative of cracking of the substance of the vessel wall occurs. The pressure, temperature or duration of treatment is reduced if the diameter of the vessel increases by about 25% or more in less than about 0.5 seconds. Monitoring the progress includes monitoring the inflation of the balloon by fluoroscopy. Monitoring the progress includes monitoring the change in pressure in the balloon.

In preferred embodiments, a balloon is provided having a diameter substantially the same as that of healthy portions of the vessel. A balloon is provided having an axial length slightly greater than the axial length of the region. A balloon is provided with means for $I^2R$ heating of the inflation liquid.

In many respects, the invention is conceived as an improvement over any prior art method of treating stenoses with heat that strives (solely by prior experiment) to predetermine a proper dose of heat and pressure to be applied. The heterogeneous nature of stenoses, e.g., differences between different stenoses and within a stenosis, generally prevents application of a predetermined heat treatment since, for some stenoses the predetermined amount is excessive, tending to damage healthy tissue, while for others it is insufficient, resulting in incomplete dilatation.

An advantage of the invention is that dilatation of stenoses is made possible using a minimum amount of heat and pressure for the tissue under treatment, as determined by the physiological response of the tissue itself. This "low stress" approach allows effective dilation while reducing the risk of undesirable side effects, such as formation of detrimental cracks or fractures or thermal damage. The use of such controlled heat and pressure as described herein reduces the amount of mechanical stress and disruption in the tissue being treated, thereby reducing the potential for post treatment restenosis and reocclusion.

In general, the treatment procedure of the invention may incorporate one or more of the following steps.

1. The practitioner chooses a liquid fillable, heatable balloon with an inflation diameter that approximates the diameter of the healthy vessel adjacent the occlusion (the size choice is similar to conventional angioplasty). In addition, it may be desirable to select a balloon having a length slightly greater than the axial length of the stenosis to be treated, to provide a smooth transition of the treated region to the healthy region.

2. The balloon is inflated to sub-dilation pressures before initiating heating. A typical sub-dilatation pressure is one to two atmospheres, however, the actual pressure will depend on factors such as balloon size. In any case, the pressure is selected such that vessel widening is not visible to the naked eye under normal conditions when observing the operation by fluoroscopy. Vessel widening under these conditions is generally less than 10% and usually less than 5% increase in lumen diameter. The low pressure inflation enables the balloon to contact the occlusion, with a good heat transfer relationship.

3. The temperature of the balloon may be increased, for example, to about 60° C., but generally not higher than 70° C. The increase from body temperature, 37° C., occurs over about 5 to 10 seconds (slow compared to laser or rf heating) permits accurate control and is generally accomplished by turning the heater on and allowing it to follow its normal heat-up curve. The exact length of time of the balloon heat-up is dependent upon the size of the balloon and heater, etc. In some cases, heating to lower temperatures, for example, 50°

C., produces movement of the occlusion. Full dilatation is usually achieved at temperatures of between 60°–65° C. The temperature may be monitored by the heated balloon multiplex technique in which energy is supplied and a thermistor monitored on a time-sharing basis.

4. The temperature may be held at about 60°–65° C. for up to 60 seconds (e.g., about 10 to 15 seconds) while the operation is monitored by fluoroscopy and/or by monitoring the pressure within the balloon. Within this "hold" period the lumen remodels to a fully dilated state where the balloon takes on its normal inflated shape. The use of a balloon filled with a liquid that is heated which in turn heats the tissue wall in contact with the balloon by conductive heat transfer is advantageous because the heating of the plaque is affected by direct conduction and convection (the latter allows heated plaque to move which allows heating of underlying plaque). This enables careful control over the heat input to the tissue, the temperature at the surface of the tissue and the rate at which the temperature is raised. The operator may monitor the rate of movement of the tissue, for example, fluoroscopically or by observing pressure changes in the balloon when a constant balloon volume is maintained. Slow changes, which may be for example, a balloon pressure change from 2 atmospheres to about 1.5 atmospheres over the course of 2 seconds also indicates that the lumen is being dilated in a gradual way to avoid cracking or other deleterious effects of excess heat or pressure stress. Fast changes, which may be in some cases, the same pressure change occurring in less than about 0.5 seconds, are often undesirable because they indicate excessive stress on the lumen. In response to such a fast change, the operator can suspend heating or pressurizing the balloon.

During the course of the treatment, while observing the effects fluoroscopically, and/or through monitoring the pressure in the balloon, the operator has the option of increasing or decreasing the temperature or pressure or the duration of treatment in response to the observed effects on the tissue. Thus, low stress temperature and pressure profiles can be implemented by the practitioner so that the treatment is tailored to the physical characteristics of the particular nature of the plaque encountered.

5. After the vessel is fully dilated, the balloon heater is turned off resulting in the balloon temperature falling off in a gradual way allowing time for stress to be equalized. The balloon remains inflated during this cool down period which may last about 15 to 30 seconds. The balloon may also be cooled by circulation of a cooling liquid therein.

6. The balloon is deflated and removed.

7. The procedure, steps 1–6, may be repeated without removal of the balloon, although this is generally not necessary since the lumen after treatment exhibits smooth surfaces and has a diameter substantially the same as the healthy tissue adjacent the occluded area, both of which factors may inhibit reocclusion which may be either acute, resulting from a flap closing or clot formation; mid-term reocclusion in the 6 month range which can result from restenosis or scar tissue response; or long term reocclusion over a year to 18 months later which results from failure to properly treat the underlying disease.

The principle behind various aspects of the invention is to use the lowest possible stress to produce dilatation of a stenosed or occluded lumen, and to achieve this by use of a thermal balloon whose heating, preferably by conductive heat transfer, is closely controlled. Low stress is achieved by applying relatively low temperature to soften the plaque so only relatively low pressures (1–2 atm) are necessary to remodel it to the desired size. The combination of heat and pressure is below that which causes significant post-operative platelet deposition. The type of side effects that occur when excessive stress is placed on the system include lumen responses such as clotting, intimal proliferation (scarring) and hormonal changes which cause restenosis. Longer term effects include the formation of aneurysms (weakening or thinning of the vessel wall).

Plaque is a heterogeneous material, sometimes non-living, that varies widely and may include calcified, wax-like, fibrotic, and brittle components. Many components are polymeric in nature and for remodeling such a material into a desired shape, in this case, the smooth shape of healthy lumen tissue, the plaque may be heated as a polymer resin in an extruder. The heat is applied using a liquid filled heated balloon to provide a thermal profile which enables the material to shape-change on heating in allowing stress equalization. The cooling profile similarly is important in determining the characteristics of the remodeled plaque For example, cooling too quickly can produce a brittle material.

In the invention, the heat is preferably applied to the tissue by conduction from the wall of the balloon. The hottest part of the plaque is that which is in contact with the balloon surface. As the plaque is heated, thermo-plastic components soften causing, under the pressure application, an axial and radial shift in the position of the occluding material, filling in any unevenness and effectively displacing the plaque to expose new surface that is in turn heated and remodeled in the same way. The result is a lumen having smooth interior walls and a diameter approximately equal to the diameter of the lumen defined by the adjacent healthy tissue without substantial radial movement of the tissue upon which the occluding material was deposited.

This improved understanding of the softening behavior of different types of plaque as discussed herein helps determine the optimal technique for choosing balloon size, temperature, time and pressure. By monitoring the balloon pressure decay curve as the vessel responds to heat, the operator can tune or "titrate" the additional time, heat and pressure necessary to increment these variables to the best result. For example, a very fast decay could indicate a split or crack, a medium speed would suggest a melting "realignment" and a slow decay would suggest a slow remodeling. If the applied pressure were removed and the balloon pressure rose, it would suggest the presence of elastic recoil. In addition, by monitoring this process with intravascular ultrasound (IVUS) from an adjacent vessel and doing a "frame by frame" replay, the melting and remodeling taking place may be observable.

Other aspects and advantages are discussed in the following description and in the claims.

DESCRIPTION OF THE PREFERRED EMBODIMENT

We first briefly describe the drawings.

Drawings FIG. 1 illustrates schematically, a balloon catheter system according to the invention.

Structure

Specific details of the construction of a heated angioplasty balloon can be found in the parent to the present application, U.S. Ser. No. 263,815, filed Oct. 28, 1988, the entire contents of which is hereby incorporated by reference.

Figure 1:
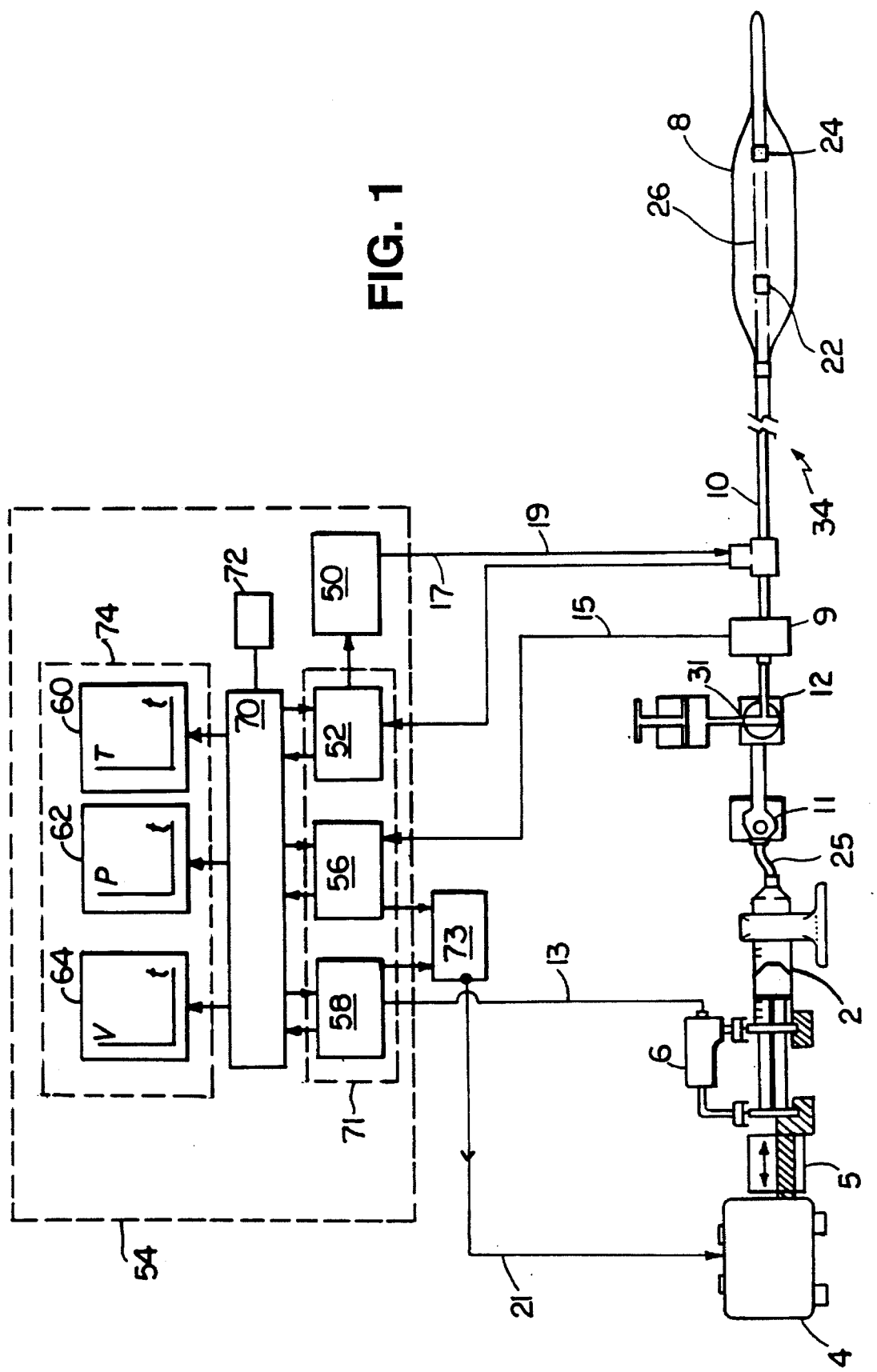
Figure 2:
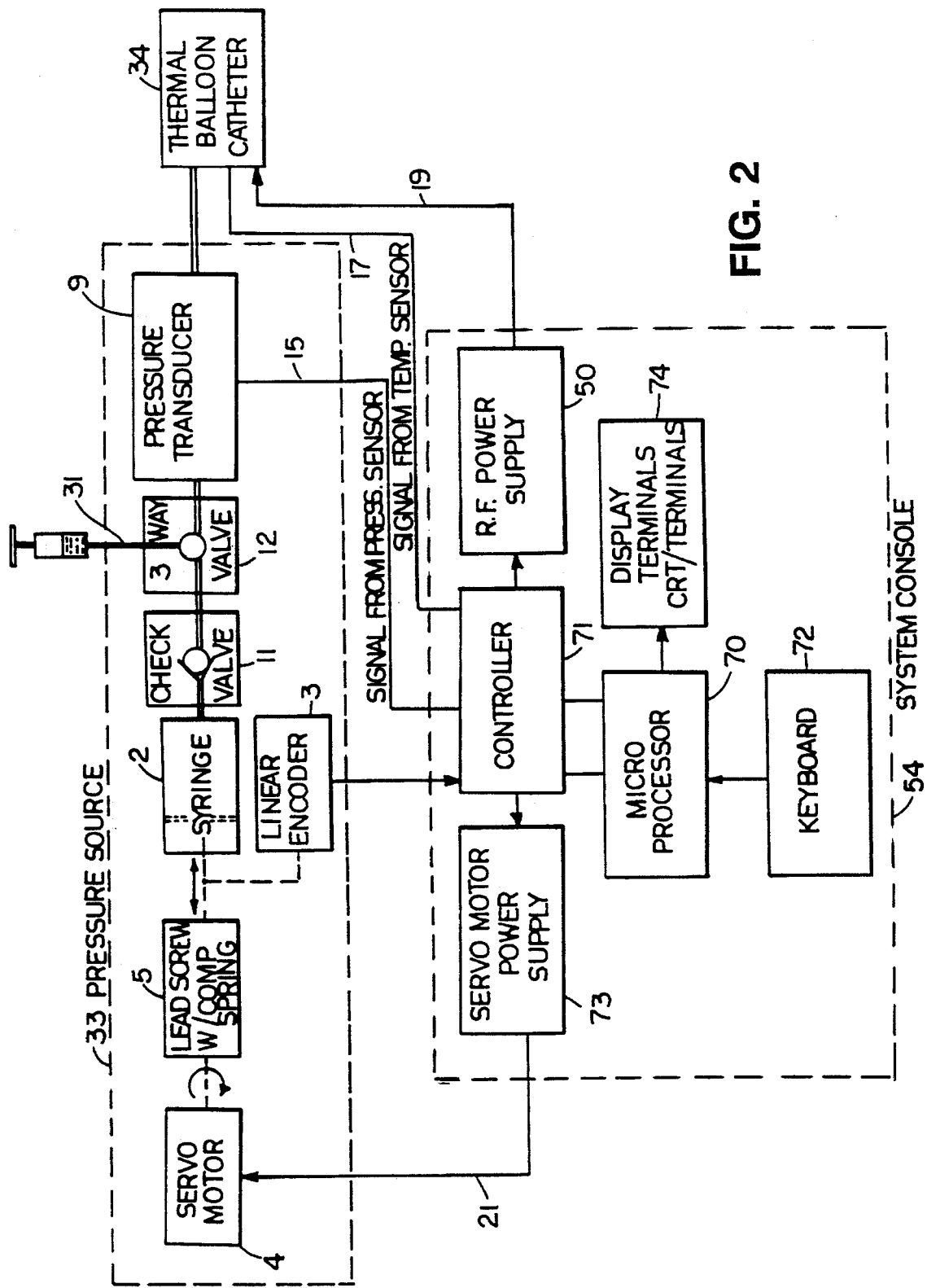
FIG. 2 is a block diagram of a system for physiologically controlled remodeling according to the invention.
Figure 3:
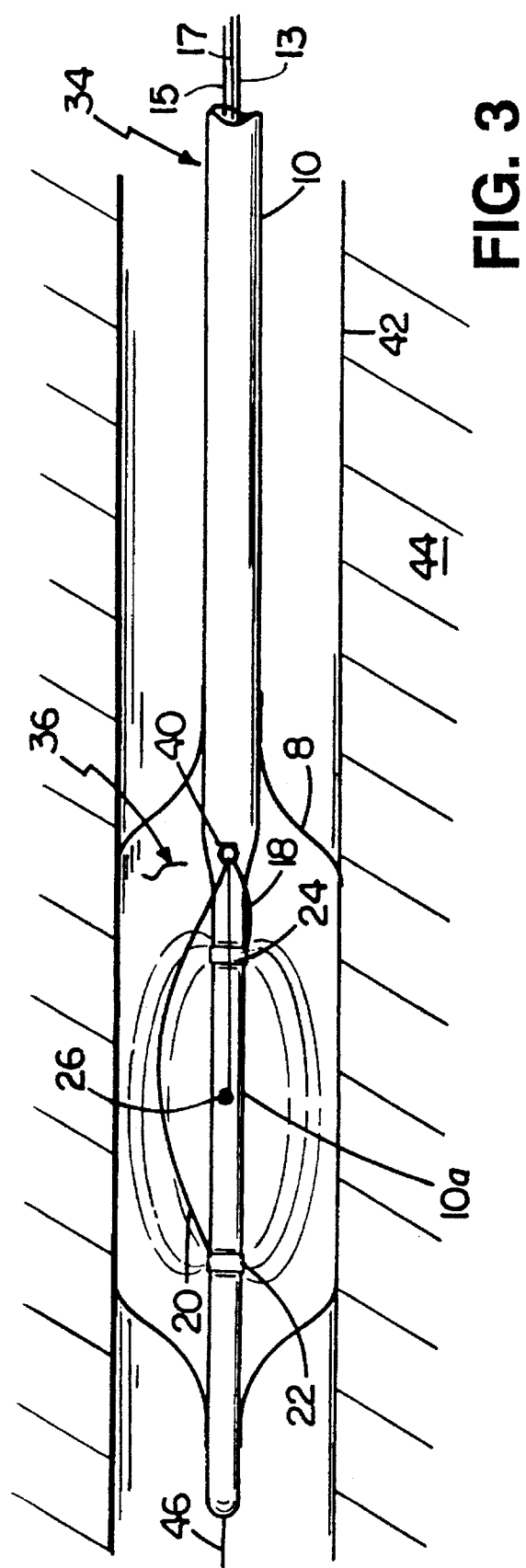
FIG. 3 is a balloon catheter blown up and cutaway to show details of the balloon.

Referring to FIGS. 1 to 3, a balloon catheter apparatus 34 includes a nondistendable (substantially inelastic) inflatable balloon 8 (for example, polyester) at the end of a catheter shaft 10. The apparatus also includes a pressure source 33 with a syringe pump 2 which may be a syringe pump as illustrated, driven by a controllable double acting displacement servo motor 4 including a lead screw and a compression spring assembly 5. Servo motor 4 provides rotary motion to drive lead screw 5 which translates the rotary motion into a linear motion and converts motor torque into a linear force. Linear force is applied to syringe 2 via a compression spring (not shown) and converts the linear force into fluid pressure, the syringe being filled with saline or conductive contrast medium which is communicated to the catheter balloon 8. Check valve 11 prevents flow of fluids from the balloon catheter to the syringe 2. The compression spring, between the lead screw and syringe, increases pressure control resolution. In some embodiments, the pump is adapted to maintain a designated pressure and may be, for example, a spring fed plunger in a syringe or microprocessor controlled pressure regulator. For inflation, fluid passes from the syringe 2 through a line 25, one way check valve 11 (such as a ball check valve), three way valve 12, pressure transducer 9 and through an inflation lumen within the catheter 10 that communicates with the interior of the balloon 8. Inflated balloon volume is measured by measuring the piston displacement with displacement transducer 6. Linear encoder 3 (FIG. 2) is mechanically coupled to the syringe plunger to sense the position of the plunger as indication of balloon volume. Linear encoder 3 processes signals indicative of the plunger position to, for example, convert signals to the rate of volume change or derivative rate of volume change. Three way valve 12 connects between the pressure transducer 9 and the check valve 11 and includes a port 31 which is used for priming and deflating the balloon with a second syringe 38.

Referring particularly to FIG. 2 (—Electrical, ---- Mechanical, and = Hydraulic systems being indicated), the apparatus has a control module 54 with a controller 71 which controls a servo motor power supply 73 and rf power supply 50. A processor 70 sequences treatment events according to program algorithms coordinated with feedback from temperature, pressure and volume sensors. Keyboard 72 allows the user to enter treatment parameters and patient data. A display 74 CRT, printer, strip chart recorder, is also provided. In a preferred embodiment, the controller 71 drives the rf power supply 50 and servo motor power supply 73 according to feedback from the temperature sensor in balloon catheter 35 (via wire 17) and pressure transducer 9 (via wire 15). Controller 71 is an analog feedback device that adjusts the signal to the power supplies according to the signal from the temperature sensor or the pressure sensor. The set point is provided to the controller by processor (microprocessor) 70 and the controller attains that set point based upon feedback. For example, if the signal from the temperature sensor (along line 17) shows the temperature is lower than the set point, controller would increase the rf power being fed to the thermal balloon catheter but if the temperature sensed indicates a temperature higher than the set point then the controller would operate in the opposite direction and would decrease the power being supplied by power supply 50. The system operates in similar fashion with regard to the pressure or the volume controller. The set point is provided by the microprocessor and the controller controls the direction and force applied to the servo motor to achieve that set point. (The balloon inflation may be controlled by the pressure controller or the volume controller.) Processor 70 includes the software that will adjust the control of both pressure and temperature. The pin connector of the inflatable catheter wiring to the console 54 includes a binary code to identify itself to the processor which, on the basis of such identity, and pre-established specifications, determines the control parameters, algorithm, etc. to control the treatment.

To use the system, the catheter is sized to, for example, match or oversize up to 20% (typically about 10%), the diameter of the adjacent undiseased vessel. The balloon is connected fluidly to the pressure transducer 9 and the syringe 2 is filled with either saline or conductive contrast medium or a combination and attached and connected (as shown). Second syringe 38, partially filled, is attached to the three way valve vertical port 31. The valve 12 is set for communication between port 31 and the expandable catheter. In repetitive fashion, the plunger of syringe 38 is withdrawn to draw air out of the catheter 34 and then pushed forward to remove air from the catheter balloon and prime the lines between. The three way valve 12 is next adjusted to allow communication between port 31 and the syringe and check valve. The priming is repeated. This process displaces air and primes the connecting tubing for accurate volume measurement during operation. The three way valve 12 is then adjusted to allow communication between the syringe 2 and the deflated catheter 34. The balloon is positioned via guidewire to the point of treatment and pressure exerted to fill the balloon to a predetermined pressure low, subdilatation pressure dictated by the program algorithm or user input. The processor cycles the pressure and temperature according to the program algorithm.

Referring particularly to FIG. 1, control module 54 includes within a servo motor power supply 73, an rf power supply 50, temperature control and detection circuit 52, pressure control and detection circuit 56 and volume detection circuit 58. The module 54, further includes readouts, 60, 62, 64, for balloon temperature, pressure and volume, respectively. The readouts allow the operator to monitor the physiological response of the tissue under treatment and tailor further treatment as required, and as will be further explained below. Connecting lines 13, 15, 17, 19, 21, deliver signals indicative of volume, pressure and temperature and transport commands and power to the proper elements for controlling each of these parameters. Line 13, connects to displacement transducer 6 for monitoring inflation volume; line 15 connects to the pressure transducer 9 for monitoring pressure; line 17 connects to a temperature sensor 26 in balloon 8; line 19 delivers power to rf heating contacts 22, 24 in the ballon 8; line 21 connects to the motor 4 for delivery of inflation fluid, and line 23 controls check valve 11. The module 54 includes internal wiring and microprocessor elements as required for control of the apparatus as discussed below.

Balloon catheter 34 includes a balloon 8 (e.g. polyethylene terephthalate, PET) mounted on nylon catheter shaft 10. The fully extended diameter of balloon 8, when inflated, ranges from 2 millimeters for coronary vascular procedures, to 20 or 35 millimeters for treatment of the prostate, esophagus or colon. The volume of the balloon ranges from ⅛ cc for the smallest balloon to 100 cc for the largest balloon. The wall thickness of balloon 8 is about 0.001 inch. Guidewire 46, which can extend past the distal end of the catheter, may be used to guide the catheter through the vascular system or luminal structure. Balloon 8 is fillable with an electrically conductive fluid 36 such as normal saline (0.9 percent NaCl in water), a conductive radiopaque fluid, or a mixture of saline solution and a radiopaque fluid. A valve (e.g., check valve, a ball check valve with a downstream vent) may be provided in the inflation fluid plumbing to avoid backflow when the balloon cools down after treatment (the backflow is caused by a slight shrinking of the artery, which increases the pressure within the balloon). The exterior of the balloon is coated with a non-stick coating having a low coefficient of friction, such as silicone or polysiloxane.

Annular electrical contacts 22 and 24 inside of balloon 8 are bonded directly to the catheter shaft. The spacing between the contacts is approximately half the length of the balloon, and the spacing from the respective end of the balloon is approximately one fourth the length of the balloon, so that the balloon will heat evenly. The contacts 22 and 24, connect to opposite poles of current-controlled (constant current) radio-frequency power supply 50 in the control module 54. The balloon also includes a thermistor 26 for measurements of balloon temperature. Wires for the contacts and thermistor are enclosed within catheter shaft 10 along its length, and exit catheter shaft 10 through a lumen, 40 which is accessible from inside of balloon 8.

Rf power supply 50 preferably operates at 650 kilohertz, but can be at any frequency within the range of about 100 kilohertz to 1 megahertz. The fluid 36, while selected to have resistive losses, has an electrical impedance low enough that it will conduct the current supplied by rf power supply 50 at voltages of about 100 volts or lower, so that there will be no arcing across insulated wires 18 and 20.

The balloon thermistor 26 connects with temperature control means 52 which includes a circuit that permits manual or automatic control of the internal balloon temperature and can preferably be programmed to carry out a temperature algorithm that varies as a function of time. As will be discussed further herein, useful programs include step programs and programs allowing linear or nonlinear increase of temperature. Temperature display means 60 is responsive to the temperature control 52 and is preferably a CRT display or alternatively a strip chart recorder which allows monitoring of measured balloon temperature as a function of time.

The pressure control means 56 allows manual or automatic programmed control of the pressure of fluid within the balloon by control of the power supply powering the servo motor. The pressure is monitored by the transducer positioned in an inflation fluid conduit, downstream from the inflation pump. The pressure can be viewed by the user on a display 62 (CRT screen or a strip chart recorder).

The volume control means 58 also includes a circuit arranged to control the power supply of the servo motor to deliver fluid to the balloon. The balloon volume inflation thus can be controlled either through the pressure controller or volume controller. The volume control means 58 monitors the volume of fluid passed to the balloon during inflation or deflation (by, for example, monitoring a servo motor pump or the displacement of a syringe pump). The volume of the balloon may be displayed graphically as a function of time on volume control means 64 (strip chart or CRT).

Operation

Figure 4:
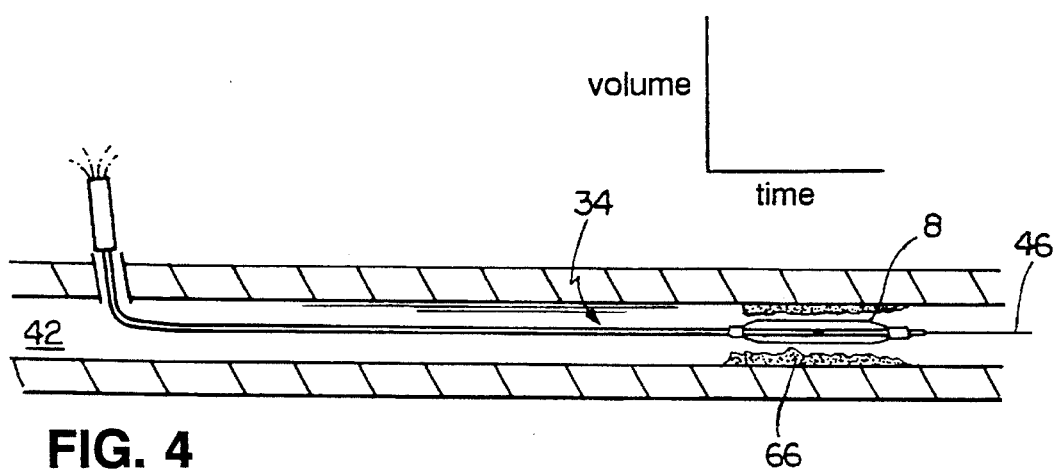
FIGS. 4–4d illustrate dilatation of an obstructed artery.
Figure 4A:
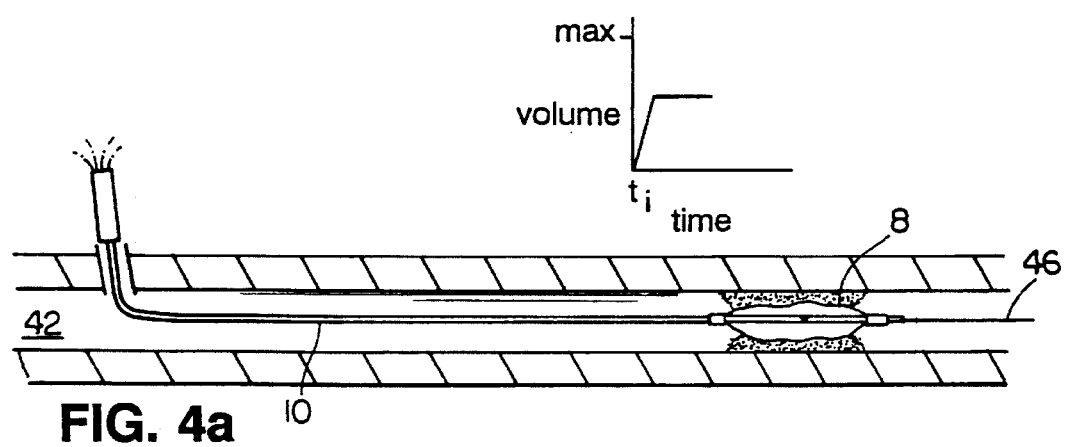
Figure 4B:
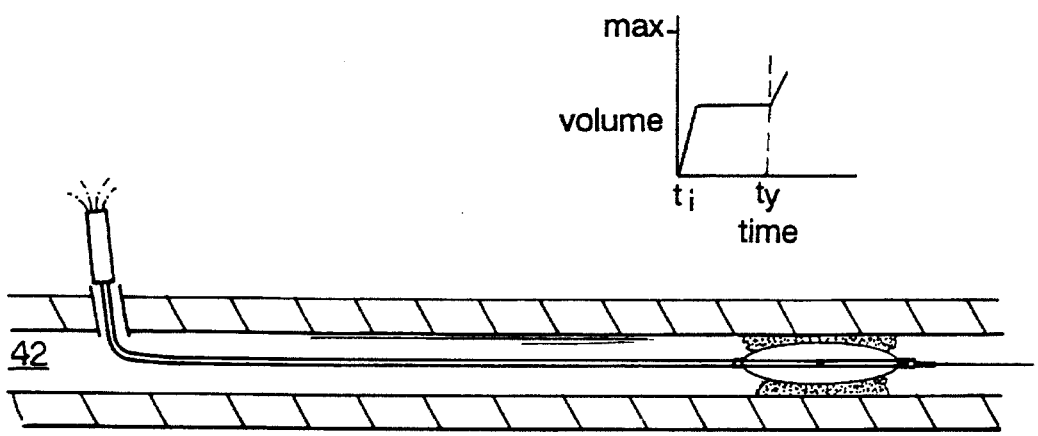
Figure 4C:
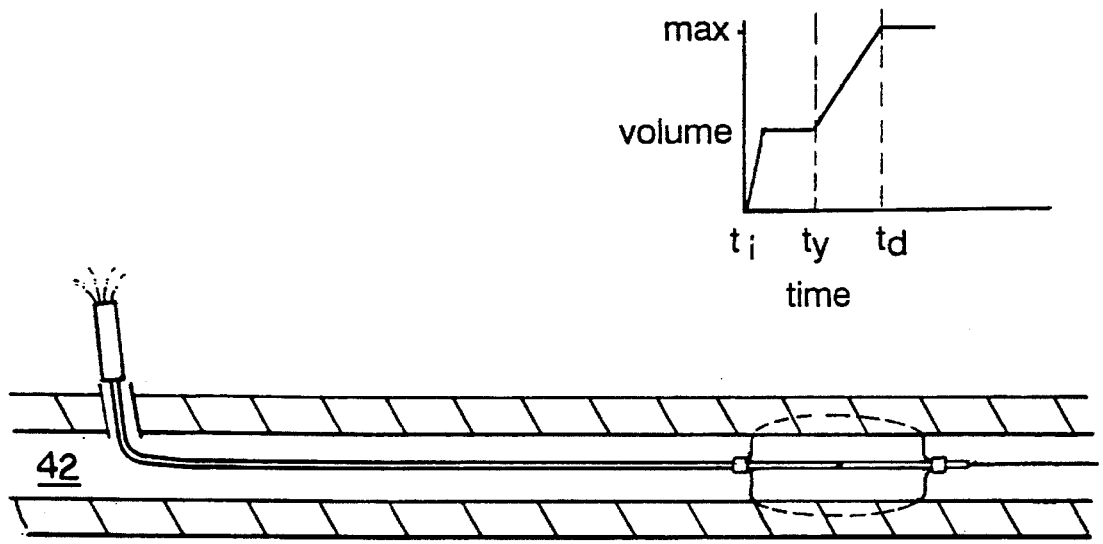
Figure 4D:
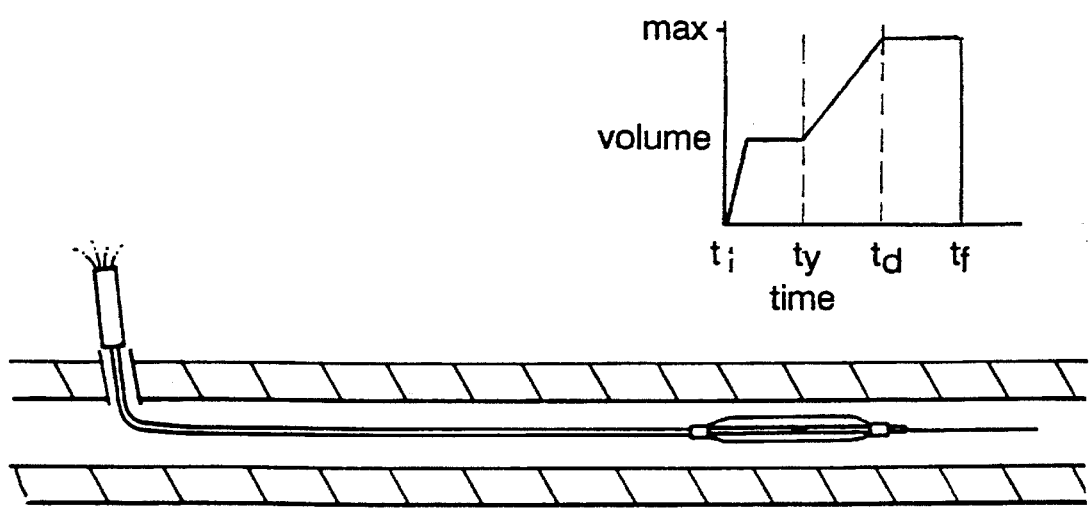

Referring to FIG. 4–4d, balloon catheter 34 is used as a heat and pressure source to, for example, dilate a blood vessel by molding the wall or an obstructing material (like plaque). The balloon volume as a function of time, during the course of the treatment is illustrated in the graph above each figure. The blood vessel may be a coronary artery, or a peripheral artery such as an iliac, femoral, renal, carotid, or popliteal artery. A percutaneous insertion is made with a needle, and guide wire 46 is introduced into the blood vessel 42. Balloon catheter 34 follows the wire 46 and is positioned at an obstruction in the artery such as a plaque deposit 66 (FIG. 4).

The balloon 8 is inflated to engage the plaque material 66 forming the obstruction (FIG. 4a), but the pressure in the balloon is kept below the normal pressure required under ambient conditions to widen the vessel to avoid cracking the plaque. Normal dilation pressure means the minimum pressure at which an unheated balloon causes substantial dilation of the respective lumen. The low, subdilatation pressure used initially to engage the plaque material may be, for example, about two atmospheres. In the case of angioplasty, normal dilation pressure is of the order of 5 to 10 atmospheres (varies with balloon size). The balloon self-forms around the irregular surfaces of the obstruction and provides a firm contact for efficient and even transfer of heat. As the occlusion yields (by virtue of heating and gentle pressure as described below), the balloon expands to maintain even contact with the surface and the pressure falls. The control system monitors the pressure, and temperature and volume of the fluid in the balloon as a function of time to determine various physiological conditions and responses to treatment, while the user may visually monitor the parameters.

If balloon 8 contains conductive radiopaque fluid, the location of balloon 8 can be monitored also by means of fluoroscopy. Balloon 8 is inflated through an internal lumen of the catheter with either saline, a conductive radiopaque fluid, or a mixture of saline and a radiopaque fluid. The type and conductivity of the ionic fluid in the balloon is chosen to optimize the conversion of rf energy into heat. ($I^2R$ loss, see U.S. Ser. No. 263,815, incorporated, supra). The system is operable over typical pressures in the range of less than 1 to 17 atmospheres.

With balloon 8 inflated to a low level of pressure and engaging the obstruction, the user (or program) initiates the bi-polar heating between the electrodes 36 (e.g. by depressing a footswitch to start a heating program). Heat is dissipated into the fluid according to the formula $P=I^2R$ where P is the power that is dissipated into the fluid, I is the current that is passed through the electrodes, and R is the resistance of the fluid. The heat from the fluid is conducted across the balloon wall into the surrounding tissue 44. The fluid will heat to the temperature set by the user or carry out a temperature algorithm. The temperature at the balloon surface ranges from 45°–90° C. and is typically from 50° to 70° C., sometimes preferably, around 60°–65° C. The higher temperatures in the range are used for relatively thick diseased areas, where heat conduction out of the target tissue is high or where deeper penetration or therapeutic effect is desired. Heating will continue as the time/temperature algorithm dictates or until the operator deactivates the program. Typical treatments in the coronary artery take 15 to 60 seconds including a 5 second temperature increase and ten seconds to reduce the balloon temperature prior to deflation and removal.

While heating, the operator may monitor the condition and physiological response of the vessel under treatment, particularly by observing the volume and/or pressure of the balloon. When the obstruction is under certain conditions of heat and pressure, the heterogeneous plaque material (usually including fat, fibrogen, calcium) softens, resulting in a sudden change in the allowable volume of the balloon at a given low pressure (below the pressure needed to crack the obstruction). Analogous to a thermoplastic material, the heat, decreases the yield stress of the plaque and artery under treatment to the point where the stress induced by the balloon exceeds the yield stress thereby causing a sudden change in balloon volume. The physiological response, the sudden yield of the obstruction, is detected by the system as a sudden change in the volume or pressure, or rate or change of volume or pressure.

In FIG. 4b, for example, the volume of the balloon is shown, for example purposes, to increase slowly as the occluding material elastically (reversibly) expands with gentle heating until it increases suddenly upon reaching a yield point (y) at time ($t_y$) corresponding to the conditions of pressure and temperature at which the occlusion yields. Thereafter, the volume again increases as the occluding material yields plastically (substantially nonreversibly).

As shown in FIG. 4c, after detection of the yield point, the operator determines the course of further treatment, which may include changes in temperature or pressure of the balloon, to effect full dilatation of the artery where the continued treatment leads to full expansion of the balloon and artery at a time ($t_d$).

Finally, after the vessel has been fully dilated, the temperature of the balloon is reduced, while the balloon remains inflated. Recycling the temperature allows the material of the obstruction, the plaque, to be mold-formed by the balloon as it cools and reconstitutes. The interior walls of the remodeled lumen are left smooth and with reduced chance of reocclusion. The temperature is reduced while the balloon is inflated. The balloon is deflated and removed from the body lumen (FIG. 4d).

The following examples 1–7 illustrate possible operating procedures using a fluid delivery means adapted to maintain set pressures in the balloon. It is an advantage of the invention that by feed back of physiological response during treatment, the operating procedures may be tailored for the specific condition of each patient where, for example, the nature of the occluding material (composition, location, morphology) may be different. The occlusion may be treated using the least obtrusive pressure and temperature conditions to dilate the vessel in a manner that may discourage hyperplasia of the artery and reocclusion.

Figure 5:
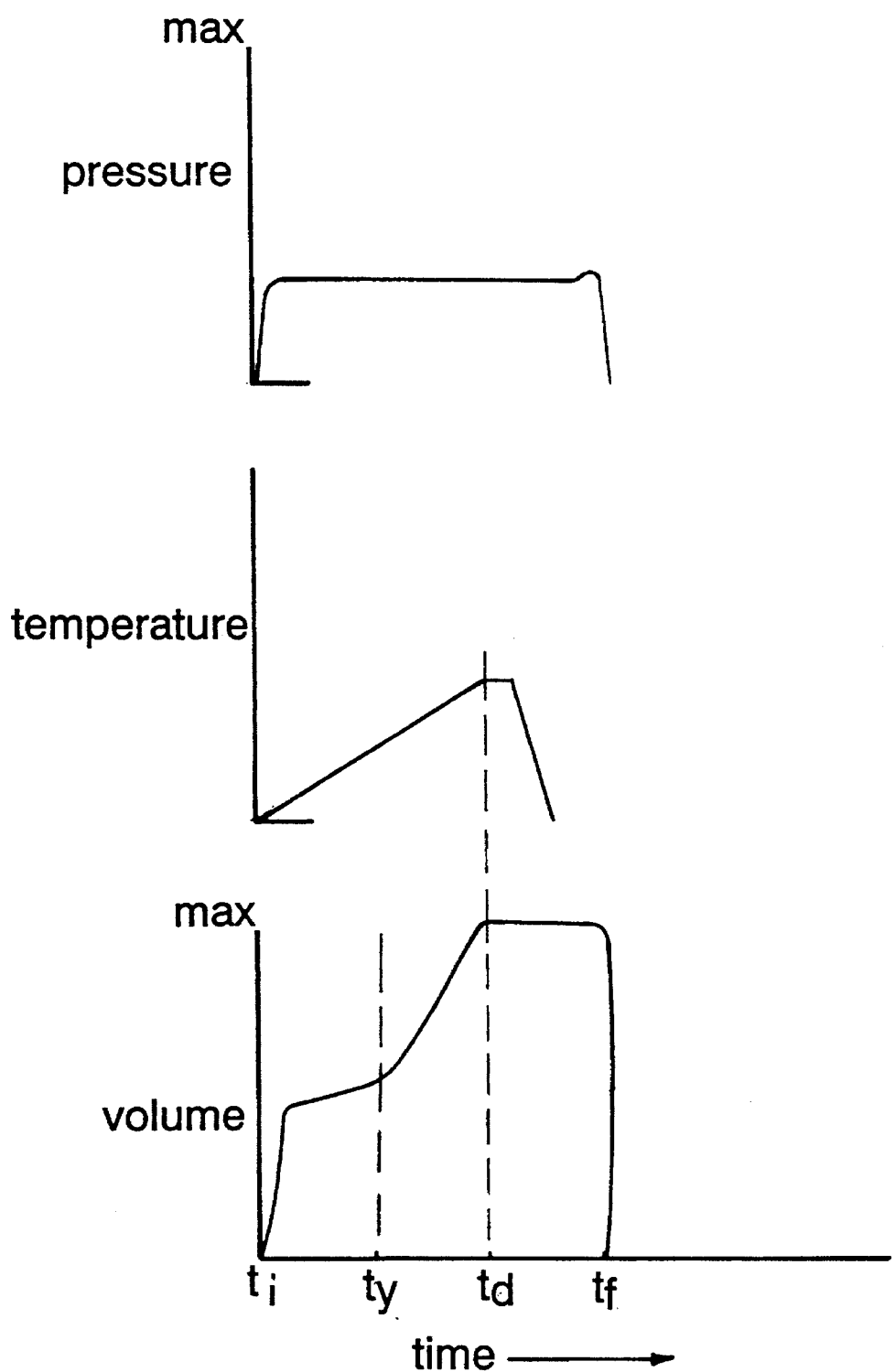
FIGS. 5–5f illustrate balloon pressure, temperature, and volume for example dilatation procedures 1–7, according to the invention.
Figure 5A:
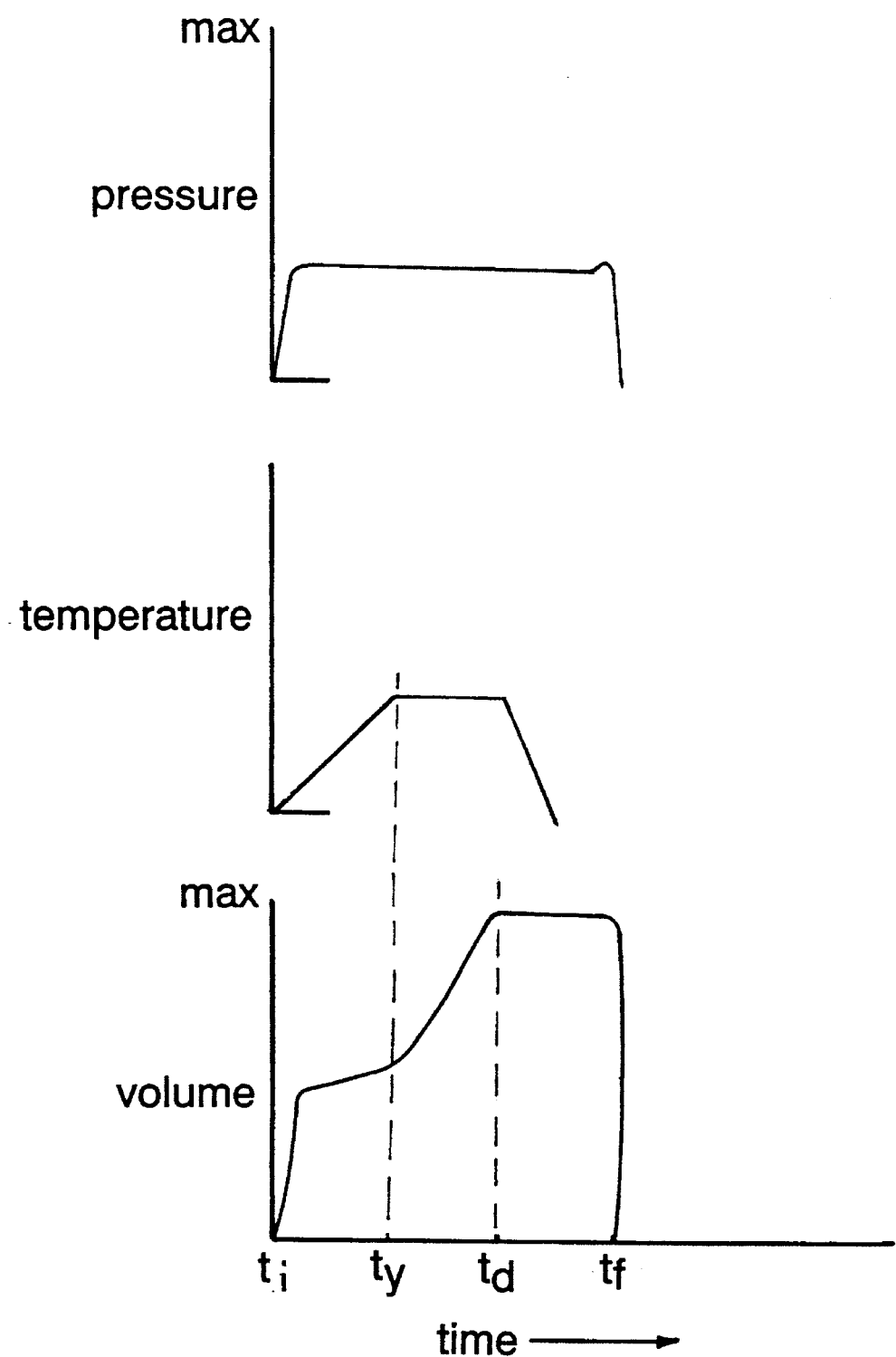
Figure 5B:
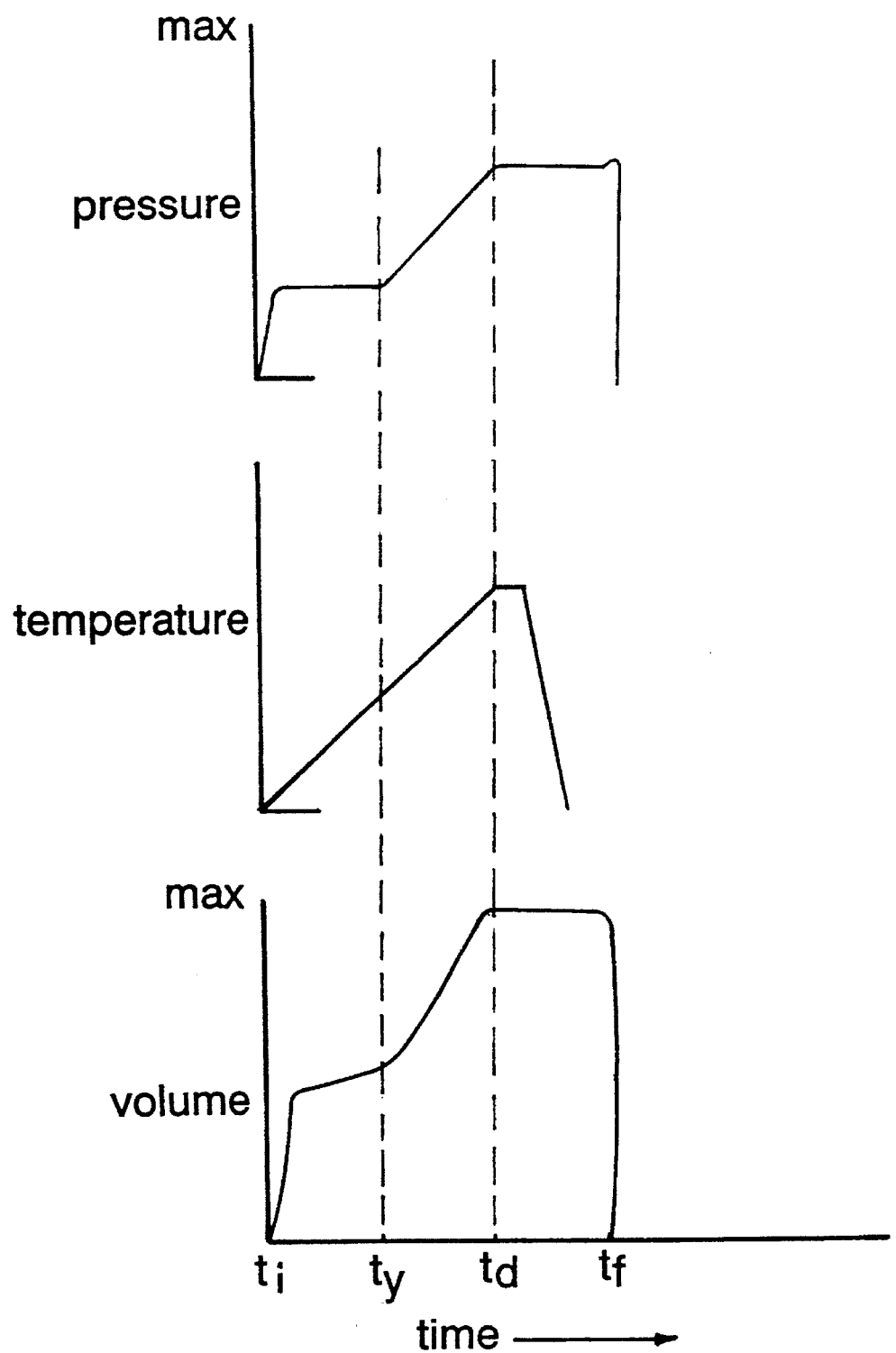
Figure 5C:
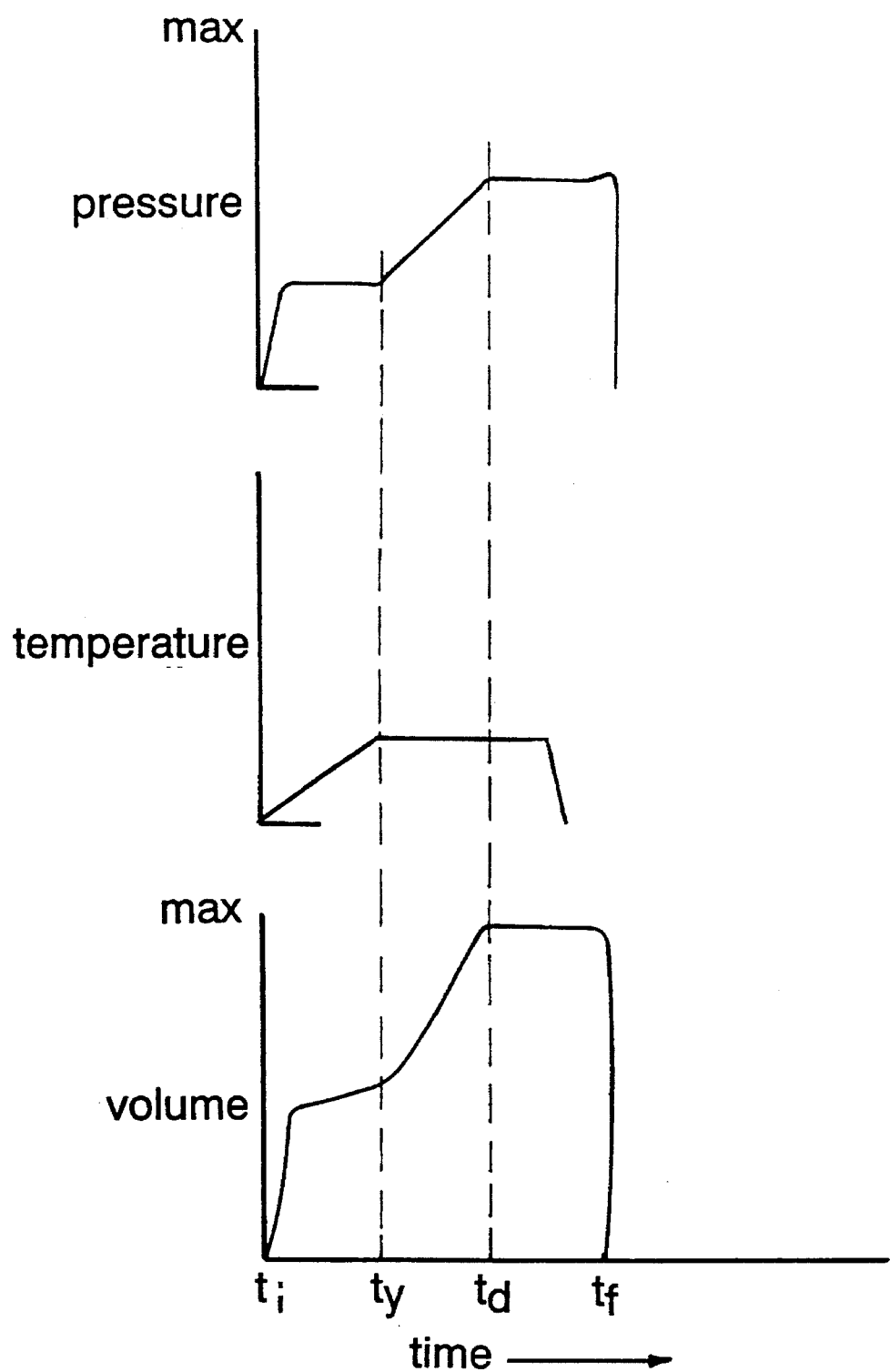

In FIGS. 5–5c balloon pressure, temperature, and volume as a function of time are indicated for the Example procedures 1–6, below. The time ($t_i$) is the initial time at which the balloon is positioned at the obstruction and inflated to contact the obstruction (but below maximum pressure, $P_{max}$, or volume, $V_{max}$). The time ($t_y$) corresponds to the time at which yield point of the obstruction material is reached. The time ($t_d$) is the time at which the vessel is fully dilated. In each of the examples, the temperature of the balloon is reduced before the balloon is deflated and removed at time ($t_f$). It will be understood that the balloon temperature decrease may be programmed to follow a path different from the symmetrically opposite (recycled) path of the temperature increase, as shown in Examples 1–7.

EXAMPLE 1

Referring now to FIG. 5, the balloon is inflated and maintained at a constant pressure by a pressure regulator over the course of the treatment. The temperature is initially increased. The volume of the balloon remains substantially constant until time ($t_y$), when the occluding material yields, and thereafter volume increases. The linear temperature program is maintained until the balloon reaches its maximum volume, at ($t_d$) indicating the vessel is fully dilated. The temperature is held constant for a short time and then reduced. The balloon is deflated and removed (As shown, as temperature is reduced, measured pressure increases slightly as the vessel contracts slightly, the check valve preventing fluid flow and therefore allowing pressure buildup.)

EXAMPLE 2

Referring now to FIG. 5a, the balloon is inflated and the pressure is held constant during the course of the treatment. The temperature is increased until the yield (ty) is detected and is thereafter held constant while the volume of the balloon expands to full dilatation volume (td). The temperature is held constant for a time after full dilation of the balloon and then reduced. The balloon is deflated and removed.

EXAMPLE 3

Referring now to FIG. 5b, the balloon is inflated, the temperature increased. The pressure is held constant until the yield is detected (ty), at which time the pressure is increased until the balloon is fully dilated (td). The pressure and temperature are held constant for a time. The temperature is then reduced. The balloon is deflated and removed.

EXAMPLE 4

Referring to FIG. 5c, the balloon is inflated to a low pressure and the temperature is increased until the yield is detected ($t_y$). Thereafter the temperature is held constant and the pressure increased until the balloon is fully dilated ($t_d$). The pressure and temperature are both held constant for a time and the temperature reduced. The balloon is deflated and removed.

EXAMPLE 5

Figure 5D:
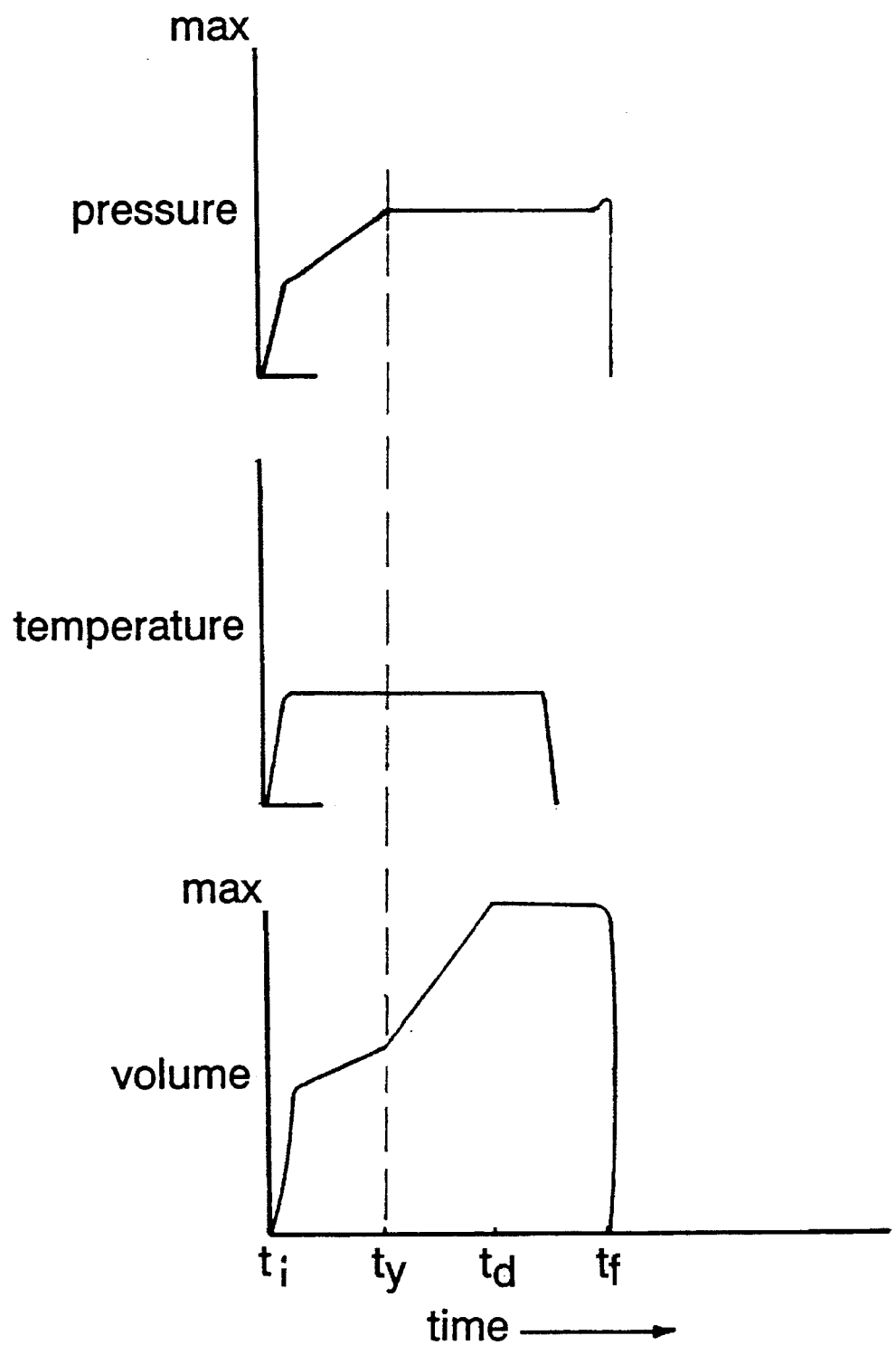

Referring now to FIG. 5d, the balloon is inflated and the temperature is brought quickly to a temperature and held constant during the course of the treatment. The pressure in the balloon is increased until the yield is detected ($t_y$). Afterwards the pressure is held constant again while the balloon inflates to its maximum dilatation volume ($t_d$). The temperature is then reduced. The balloon is deflated and removed.

EXAMPLE 6

Figure 5E:
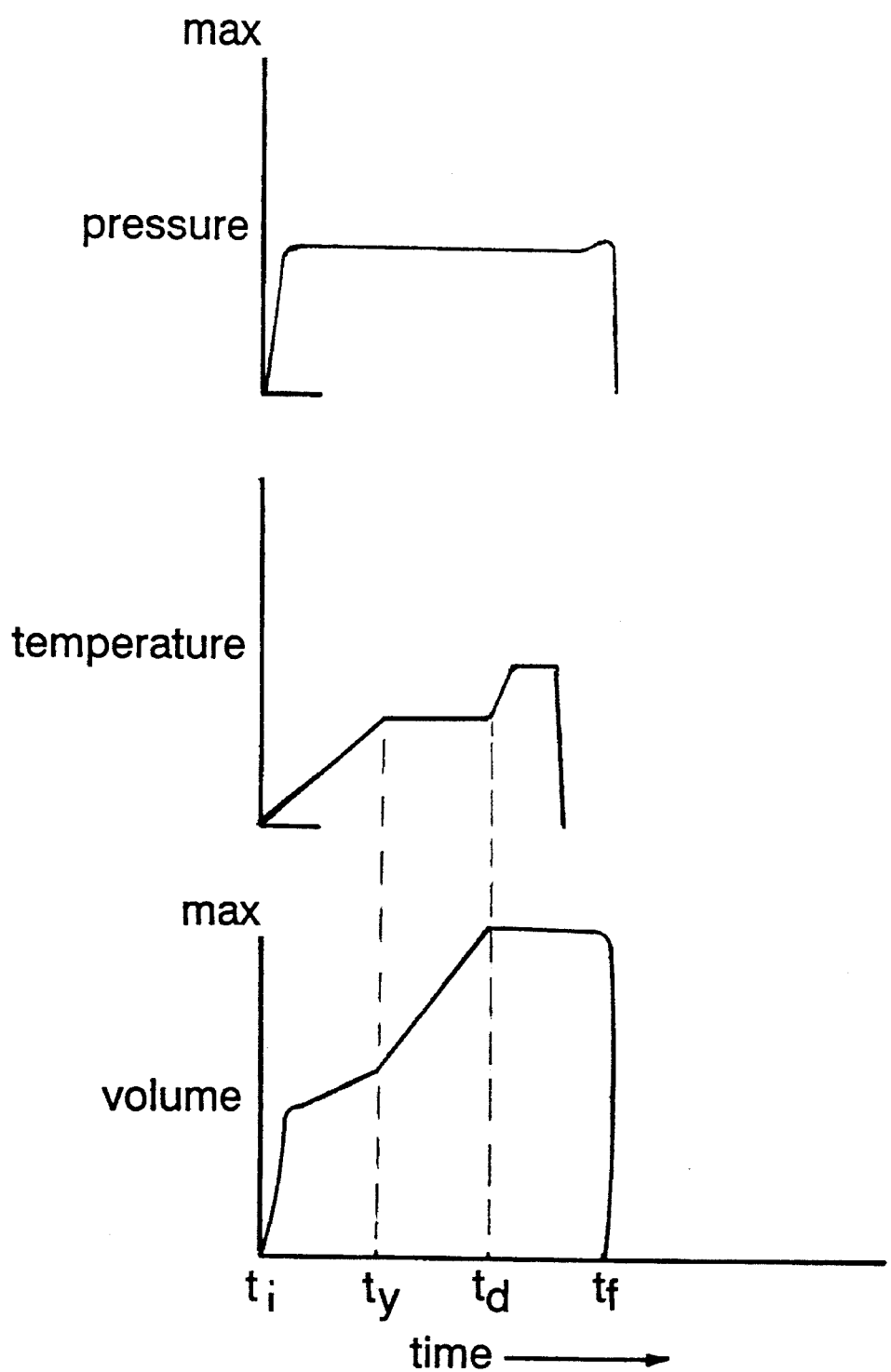

Referring how to FIG. 5e, the balloon is inflated and the temperature increased until the yield is detected ($t_y$). The temperature is then held constant until the balloon is fully dilated ($t_d$). The temperature is then increased above the yield temperature (for example, 5 degrees) and held for a period of time. The temperature is then reduced. The balloon is deflated and removed.

EXAMPLE 7

Figure 5F:
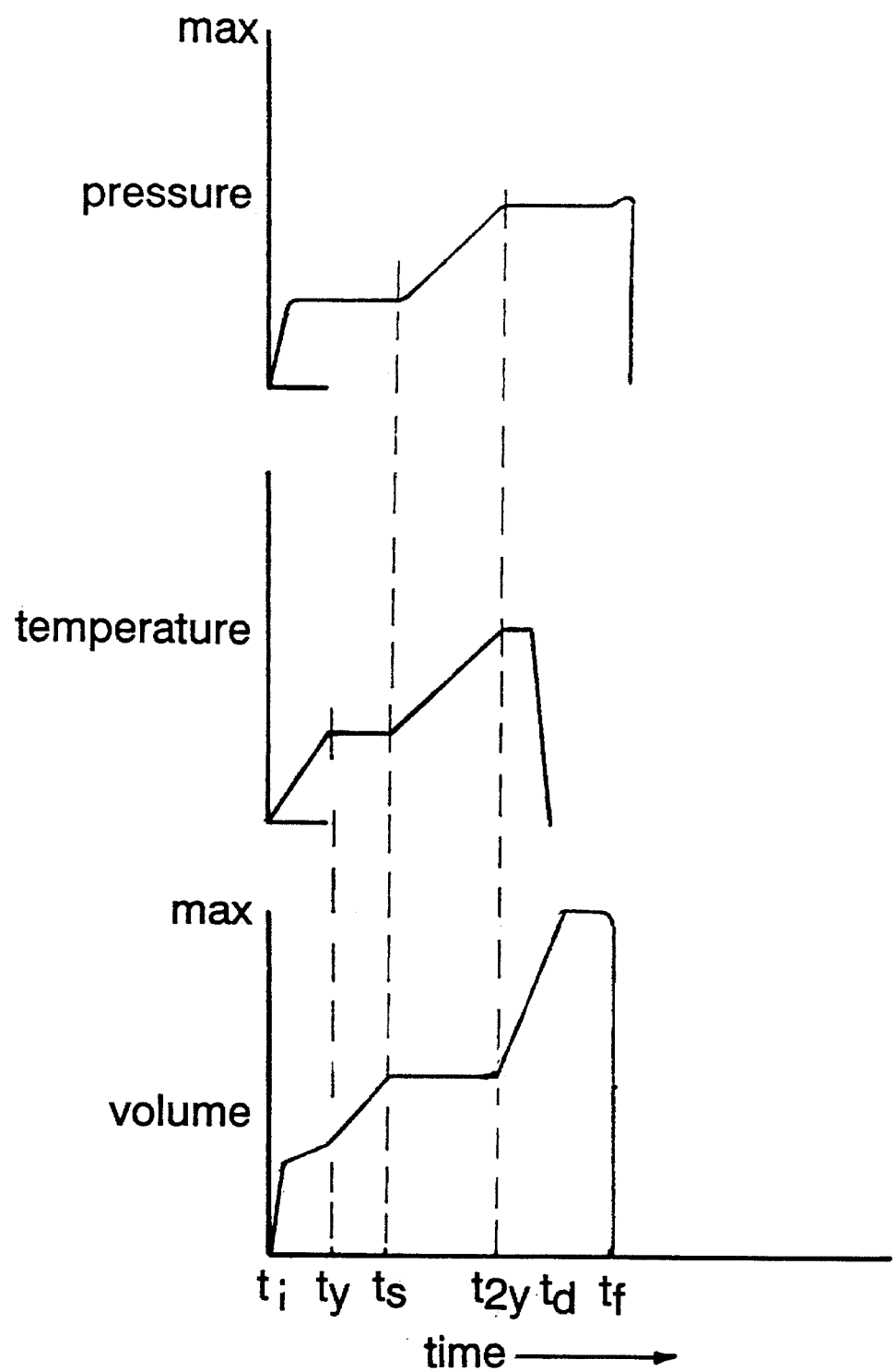

Referring now to FIG. 5f, the balloon is inflated and, initially, the pressure held constant while temperature is increased until the yield is detected ($t_y$), after which the temperature also is held constant. After the yield the volume is observed to increase until time ($t_s$) when the volume plateaus at a volume below the full dilatation volume. Upon detection of the volume plateau, the temperature and pressure are both increased until a second yield is observed at time ($t_{2y}$), after which the temperature and pressure are held constant and the balloon expands to full inflation volume ($td$). The temperature may be reduced, the balloon deflated and removed.

Example 6 demonstrates the flexibility of determining treatment based on detection of physiological response. With the apparatus and methods described herein the device may be adjusted to tailor treatment based on changing conditions during the procedure.

Other Embodiments

Operation

It will be understood that the invention may be practiced otherwise than as described herein. The principal of the invention is to allow the tissue/lesion to respond at the lowest temperature and pressure necessary to perform dilatation to minimize effects such as cracking. The tissue responds physiologically, meaning that only when the softening point is reached, will the material remodel. Although in general a yield point is detectable as described above, there may be cases where a gradual dilatation occurs without an abrupt or detectable yield point being observed. In one other embodiment, the operator monitors the pressure in the balloon after inflation with a given volume of inflation fluid to determine the physiological response to treatment. For example, the balloon may be inflated with a volume of inflation fluid such that the balloon engages the obstruction but does not dilate the lumen. (A screw cranked syringe could be used to deliver a selected volume). The obstruction is then heated and the pressure in the balloon monitored by the system. For example, the operator may inflate the balloon to a sub-dilation level, e.g., 2 atmospheres. Next the temperature is increased to approximately 60 C.—a level which is high enough to soften the plaque allowing remodeling at low pressure, but not so high as to desiccate or char the plaque. At the yield point of the material, the expansion of the balloon is detected by the system as a decrease in pressure (no further inflation fluid is delivered). After the yield point is detected, the system provides for further treatment if desired, for example, introducing more inflation fluid, adjusting the balloon temperature, etc. Additionally, the rate of decrease in pressure may be monitored on a display device to determine the condition of the lumen and the progress of treatment.

A further physiological response measured by the system could be a change in thermal characteristics of the tissue. This would be measured by change in power required to maintain a constant temperature within the balloon. A change in thermal characteristics may be measured by the diminution in power required to maintain a constant temperature within the balloon, because of a diminished thermal gradient between the balloon wall and the tissue. The power required may also be diminished by a reduction of blood perfusion through the tissue due to a coagulation of perfusion channels within. The changes in power required are sensed at the rf energy supply output, which may be fed back into the microprocessor for establishing further control.

It will also be understood that programmed increases in temperature and pressure may be linear, nonlinear or step functions. The timing of operations may be keyed to the absolute volume, change in volume or rate of change of volume of the balloon.

Heating

Additionally, it is believed most advantageous to heat the tissue primarily through conductive heat transfer by physically contacting the tissue with a controlled heating element (e.g. an rf heated balloon as described above). Plaque, tumors, intimal hyperplasia, diseased tissue, etc., are generally less vascularized, (i.e, less cooled by blood flow) than surrounding healthy tissue. Thermal conductive heating therefore provides higher specificity for heating target tissues while avoiding substantive heating (and damage) of healthy, vascularized tissue. It will be understood, however, that treatment with less specific heating means, such as heating by direct exposure of the tissue to electromagnetic radiation (heating in this case is due to non-specific absorption of photons by all tissue) or rf conduction through the tissue (which heats by inducing electric currents through electrically conductive tissue and blood) may be configured to take advantage of physiological feedback control as described herein.

The chart below compares the laser, RF surface electrodes and direct heating modes.

| COMPARISON OF DIFFERENT METHODS OF HEATING A VESSEL WITH A BALLOON | | | |
|---|---|---|---|
| | Laser | RF surface electrodes | Hot Fluid inside balloon |
| Heating Principal | Optical Absorption | Electrical Resistance ($I^2R$ loss in tissue) | Thermal Conduction |
| Control Principal | Power dosimetry (possibly acoustic feedback) | Impedance of tissue | Temperature of balloon fluid |
| Factors affecting tissue heating | | | |
| Primary | Tissue absorption | Electrical conductivity | Thermal conductivity |
| Secondary | Thermal conductivity | Thermal conductivity | Thermal mass (specific heat) |
| Implications for clinical | Heats dark tissue preferentially Heterogenous colors heat tissue unevenly Burnt tissue keeps heating Temperature is hard to control Can overheat | Heats areas of highest conductivity first . . . such as healthy tissue containing blood Plaque may not heat as well Temperature is hard to control | Heats areas that are poor heat sinks first. This includes plaque Will not overheat beyond preset temperature Healthy vessel is heated less Temperature can be precisely controlled Rate of heat rise can be |

| COMPARISON OF DIFFERENT METHODS OF HEATING A VESSEL WITH A BALLOON | | |
| --- | --- | --- |
| Laser | RF surface electrodes | Hot Fluid inside balloon |
| | | controlled |

The uniformity of the balloon temperature can be encouraged by mixing or creating a turbulence in the inflation fluid within the balloon. In one embodiment, this is accomplished by withdrawing a portion of the fluid, for example 25% of the volume, and quickly reinjecting. The reinjection can be carried out at a convenient time during or prior to heat treatment. Usually a single reinjection is sufficient to prevent temperature stratification of the inflation fluid, even for relatively large balloons of e.g., 30 mm, inflation diameter.

Additionally, the depth of the heating can be controlled by selection of balloons of different diameters. A balloon with an inflation diameter larger than the natural diameter of the lumen under treatment (the diameter without occlusion), enhances mechanical contact and compresses the obstructing material. Fluid flow, such as blood flow within the compressed tissue is also minimized. All of these factors increase the penetration depth of heat into the occluding material. With proper selection, the heating depth may be controlled to heat treat for occluding material without substantially heating or damaging the underlying healthy tissue of the lumen wall. Larger balloons, giving better contact and higher compression increase the penetration depth.

Uses

The balloons, as described, can also be used for investigations of the morphology of occlusions. In one procedure, the balloon is positioned at the obstruction and inflated to make firm contact with the occlusion but the pressure is kept below that needed for dilation. The balloon is heated, for a period, at a temperature below the yield point of the material, but high enough to mold the balloon material around the morphological features of the occlusion. Finally, the balloon is allowed to cool (while inflated) and then withdrawn. Upon reinflation outside the body, the balloon takes a molded shape (concentric, eccentric, reflective of calcified or fibrous formations, etc.) influenced by the morphology of the occlusion, and may be studied as a three dimensional model. In another procedure, the balloon is studied after dilatation as described herein. The balloon, after being dilated and cooled will take the shape of the artery post angioplasty. The topography of the artery post angioplasty is a useful indication and quantification of the success of the procedure.

It will also be understood that the invention may be used in lumens other than those of the vascular system. For example, dilatation may be performed in the esophagus, prostate, GI tract, fallopian tube, urinary tract, biliary tree, pancreatic duct, surgically constructed anastomoses or tract accesses to organs (e.g. fistulas) or any lumen constricted by plaque, intimal hyperplasia, a tumor or other obstruction.

In an alternative embodiment for monitoring the temperature of the balloon, the impedance of the saline inflation fluid may be monitored.

Other embodiments are within the scope of the claims.
What is claimed is:

1. A method of angioplasty, comprising:
   providing a catheter having a liquid-expansible dilatation balloon and means for controllably providing heated liquid within the balloon to enable conductive heat transfer from the heated liquid, through the wall of the balloon,
   inserting the catheter into a region of a blood vessel narrowed by plaque or stenotic tissue,
   inflating said balloon to an initial subdilatation pressure sufficient to cause the balloon to engage the wall surface of the narrowed vessel in a conductive heat transfer relationship without substantially displacing the wall of the vessel,
   increasing the temperature of the engaged vessel wall by conductive heat transfer from heated liquid within the balloon while controlling the inflating pressure, the temperature of said liquid within said balloon and the duration of treatment to cause a physiological response in which the heated wall of the vessel yields to said pressure of said dilatation balloon as a result of softening of the wall produced by said conductive heat transfer,
   thereby enabling dilatation of said vessel to occur under relatively low stress conditions.

2. In the method of claim 1, controlling the pressure in said balloon to about 2 atmospheres or less.

3. In the method of claim 2 is maintaining said temperature in the range of about 60° to 65° C.

4. In the method of claim 1 initially maintaining said subdilatation pressure such that the flow of blood through the vessel is substantially blocked without widening the vessel visibly to the naked eye when observing said vessel by fluoroscopy.

5. In the method of claim 1 initially maintaining said subdilatation pressure such that the vessel does not widen by more than about 10%.

6. In the method of claim 1, after dilatation of said vessel, maintaining inflation of said balloon while reducing the temperature of said balloon.

7. In the method of claim 1, increasing the balloon temperature to a final temperature between 50° C. and 70° C. within about 10 to 15 seconds of said inflation to said subdilatation pressure, and holding said final temperature for a period up to about 60 seconds, and, thereafter reducing said balloon temperature while maintaining said inflation by terminating said heating of said fluid and allowing said balloon to cool for about 15 to 30 seconds.

8. In the method of claim 1 controlling the inflating pressure to prevent said pressure from exceeding said initial subdilatation pressure.

9. The method of claim 1 further comprising monitoring the progress of said angioplasty, and controlling the temperature, pressure or duration of treatment in response to the rate of change in the diameter of said vessel.

10. The method of claim 9 further comprising reducing the pressure, temperature of said balloon or duration of treatment if a rapid change in the diameter of said vessel indicative of cracking of the substance of said vessel wall occurs.

11. The method of claim 10 further comprising reducing the pressure, temperature or duration of treatment if the diameter of said vessel increases by about 25% or more in less than about 0.5 seconds.

12. In the method of any one of claim 9 to 11, monitoring said progress by fluoroscopy.

13. In the method of any one of claims 9 to 11 monitoring said progress by monitoring the change in pressure in said balloon.

14. The method of claim 1 in which a balloon is provided having a diameter substantially the same as that of healthy portions of the vessel.

15. The method of claim 1 or 14 a balloon is provided having an axial length slightly greater than the axial length of said region.

16. The method of claim 1 in which the inflatable balloon is provided with means for $I^2R$ heating of said inflation liquid.

17. A system for dilation of a body lumen, for use with an expandable dilatation catheter constructed to simultaneously heat and apply pressure to the tissue of the lumen to expand and dilate the lumen, comprising:

means constructed to detect physiological response of heated lumen tissue to applied pressure, said means including catheter control means responsive to the detected behavior of the heated tissue to control said catheter to enable dilatation of said lumen under relatively low stress conditions.

18. The system of claim 17 wherein said means to detect physiological response is constructed to detect yielding behavior of the lumen tissue contacted by said catheter, and said catheter control means is responsive thereto.

19. The system of claim 17 wherein said means to detect physiological response is constructed to detect change in the heat transfer characteristic of the tissue contacted by said catheter and said catheter control means is responsive thereto.

20. The system of claim 17 including means that prevents contraction of said catheter during cooling of said lumen tissue following said heating.

21. The system of claim 17 wherein said catheter control means includes a microprocessor and is arranged to receive feedbacks indicative of temperature and pressure applied by said catheter, said control means adapted to regulate heating and pressure applied by said catheter on the basis of said feedbacks and an algorithm implemented by said microprocessor.

22. The system of claim 17 including timing means constructed and arranged to provide timing of the duration of the dilatation based upon the physiological response to said heat and applied pressure.

23. The system of claim 17 in combination with a catheter constructed to heat said lumen tissue by conductive heat transfer through a wall of said catheter exposed to said lumen tissue.

24. The system of claim 23 wherein said catheter is a balloon catheter fillable with an electrically conductive liquid and associated heating means for producing said heat comprises rf electrodes within said balloon and means to apply rf energy thereto in a manner to heat said liquid by $I^2R$ losses.

25. The system of claim 17 wherein said catheter is a fluid inflatable catheter and said catheter control means is an inflation control means.

26. The system of claim 17 wherein said means to detect physiological response comprises a pressure sensor constructed and arranged to sense the fluid pressure in said catheter and detect reduction in said pressure that results due to pressure-responsive yielding behavior of the heating lumen tissue, said catheter control means responsive to said detected change in pressure, to increase the volume of inflation of said catheter.

27. The system of claim 26 where said means to detect physiological response includes a volume sensor indicating change in the inflated volume of said inflatable catheter.

28. The system of claim 25 wherein said inflation control means includes a servo motor-driven syringe pump.

29. The system of claim 28 including a position transducer for measuring the displacement of said syringe pump, thereby to indicate the volume of said inflatable catheter.

30. The system of claim 25 including means that prevent deflation of said catheter during cooling of said lumen tissue following said heating.

31. The system of claim 30 wherein said means to prevent deflation is a fluid check valve.

32. The system of claim 25 further including means for measuring the temperature of fluid within said inflatable catheter.

33. The system of claim 25 wherein said catheter control means comprises a controller constructed to receive signals indicative of the pressure or volume and the temperature of said inflatable catheter, the controller constructed to control said inflation and temperature in response to said signals, for further treatment.

34. The system of claim 17 further including display means to provide a read-out indicative of the physiological response of said tissue under treatment.

35. The system of claim 34 wherein said read-out indicates pressure applied by said catheter, heating by said catheter and volume of said catheter.

36. A system for dilation of a body lumen comprising:

an inflatable dilatation balloon catheter and associated heating means arranged to simultaneously apply heat via conductive heat transfer from said balloon to lumen tissue and pressure to said tissue, and means constructed to detect physiological response of heated lumen tissue to applied pressure, said means including catheter control means responsive to the detected behavior of the tissue to control said catheter to enable dilatation of said lumen under relatively low stress conditions.

37. The system of claim 36 wherein said catheter control means is adapted to increase the inflation of said balloon in reaction to detected yielding behavior of the lumen tissue contacted by said catheter.

38. The system of claim 36 or 37 wherein said means to detect physiological response is constructed to detect change in the heat transfer characteristic of said lumen tissue and to reduce the heating on the basis of such detected change.

39. The system of claim 36 wherein said catheter control means comprises a controller under control of a programmed microprocessor.

40. The system of claim 39 wherein said program of said microprocessor is adapted to increase an inflation set point of an inflation pressure controller in reaction to feedback from said catheter indicating yielding behavior of the heated lumen tissue.

41. The system of claim 39 wherein the microprocessor is programmed to produce heating of lumen tissue at a pressure below normal dilatation pressure.

42. The system of claim 36 wherein said inflatable dilatation balloon catheter is an angioplasty catheter, carrying an inflatable angioplasty balloon.

43. A method for dilation of a body lumen, comprising:

employing a system comprising the combination of an expandable dilatation catheter constructed to simultaneously heat and apply pressure to the tissue of the lumen and to expand and dilate the lumen;

and means constructed to detect physiological response of heated lumen tissue to applied pressure, said means including catheter control means responsive to the detected behavior of the tissue to control said catheter to enable dilation of said lumen under relatively low stress conditions.

44. The method of claim 43 wherein said means to detect physiological response is constructed to detect yielding behavior of the lumen tissue constructed by said catheter, and said catheter control means is responsive thereto.

45. The method of claim 43 wherein said means to detect physiological response is constructed to detect change in the heat transfer characteristic of the tissue contacted by said catheter and said catheter control means is responsive thereto.

46. The method of claim 43 wherein said dilation is employed to remodel a lumen.

47. The method of claim 43 wherein said dilation is employ for angioplasty.

48. The method of claim 43 including terminating a step of said procedure after a measured period from the time of detection of a physiological response.

49. The method of claim 43 employing timing means constructed and arranged to provide timing of the duration of the dilatation based upon the physiological response to said heat and applied pressure.

50. The method of claim 43 wherein the initial temperature of heating is between 50° C. and 70° C.

51. The method of claim 43 wherein said catheter is a balloon catheter filled with liquid and the wall of said lumen is heated by heating the liquid, with heat transfer by conduction from said liquid across the wall thickness of the balloon to the tissue of the wall with which said balloon is engaged.

52. The method of claim 51, wherein the liquid within said balloon is electrically conductive and said liquid is heated by $I^2R$ losses as a result of radio frequency electric currents applied to said liquid.

* * * * *